United States Patent [19]

Fayerman et al.

[11] Patent Number: 5,393,665
[45] Date of Patent: Feb. 28, 1995

[54] METHODS FOR TRANSFORMING STREPTOMYCES AND OTHER ACTINOMYCETES

[75] Inventors: Jeffrey T. Fayerman, Indianapolis; Richard K. Stanzak, Poland, both of Ind.

[73] Assignee: Eli Lilly and Company, Indianapolis, Ind.

[21] Appl. No.: 833,596

[22] Filed: Feb. 10, 1992

Related U.S. Application Data

[63] Continuation of Ser. No. 229,943, Aug. 8, 1988, abandoned.

[51] Int. Cl.$^6$ .................... C12N 15/64; C12N 1/21; C12N 15/76
[52] U.S. Cl. ............................ 435/172.3; 435/252.35; 435/320.1
[58] Field of Search ............... 435/172.1, 172.3, 252.1, 435/252.3, 252.35

[56] References Cited

U.S. PATENT DOCUMENTS

| | | | |
|---|---|---|---|
| 4,752,574 | 6/1988 | Hershberger | 435/34 |
| 4,753,886 | 6/1988 | Hershberger | 435/253 |

FOREIGN PATENT DOCUMENTS

| | | |
|---|---|---|
| 141362 | 5/1985 | European Pat. Off. . |
| 209204 | 1/1987 | European Pat. Off. . |

OTHER PUBLICATIONS

Bron et al., Nbl. Gen. Genet., 179: 103–110 (1980).
Barang et al., J. Bact., 153: 200–210 (1983).
Rudolph et al., J. Bact., 165: 1015–1018 (1986).
Tevethia et al., J. Bact. 106: 808–811 (1971).
Stryor, Biochemistry, 2nd edition, Freeman and Co., San Francisco, (1981) pp. 589–590.
Zagursky et al., Gene 27: 183–191 (1984).
Cox and Baltz, 1984, J. Bacteriol. 159:449–504.
Lomovskaya et al., 1980, Microbiol. Rev. 44:206–229.
McHenney and Baltz, 1988, J. Bacteriol. 170:2276–2282.
Engel, 1987, Appl. and Environ. Microbiol. 53:1–3.
Matsushima and Baltz, 1985, J. Bacteriol. 163:180–185.
Chater and Wilde, 1980, J. Gen. Microbiol. 116:323–334.
Chater and Wilde, 1976, J. Bacteriol. 128:644≧650.
Chater and Carter, 1978, J. Gen. Microbiol. 109:181–185.
Matsushima et al., 1987, Mol. Gen. Genet. 206:393–400.
Dente et al., 1983, Nucleic Acids Research 11:1645–55.
Barany, 1982, Microbiology–1982, 51:125–129.
Mead et al., 1986, Protein Engineering 1:67–74.
Stratagene 1988 Catalog, pp. 26–32, 104–11.
Gold Biotechnology, Inc., St. Louis, Mo., Product Information Sheets for Alter-Gene TM Kit.
Pharmacia, Molecular Biology Division, Analects, vol. 13, No. 4, pp. 1–2.
Mead and Kemper, in Vectors–A Survey of Molecular Cloning Vectors and Their Uses, Rodriguez et al., Chapter, 4, pp. 85–102, Butterworths Publishers.
Cesareni, in Vectors–A Survey of Molecular Cloning Vectors and Their Uses, Rodriguez et al., Chapter 5, pp. 103–111, Butterworths Publishers.

(List continued on next page.)

*Primary Examiner*—Richard A. Schwartz
*Assistant Examiner*—Nancy T. Vogel
*Attorney, Agent, or Firm*—Richard B. Murphy; Leroy Whitaker; Gerald V. Dahling

[57] ABSTRACT

Novel vectors and methods for a single-stranded DNA mediated gene transfer system via transformation, fusion or transduction of Streptomyces, other actinomycetes, and *E. coli* using a variety of vectors. Phasmid shuttle vectors of the invention are particularly useful as single-stranded vectors that appear to bypass one or more host cell restriction systems, and thus increase the efficiency of gene transfer into highly restrictive host cell systems. New and useful vectors are provided that allow for the cloning of genes both for increasing the yields of known antibiotics and also for producing new antibiotics, antibiotic derivatives, or any other useful gene product, including a variety of mammalian protein products.

5 Claims, 12 Drawing Sheets

OTHER PUBLICATIONS

Smith, in Vectors-A Survey of Molecular Cloning Vectors and Their Uses, Rodriguez et al., Chapter 3, pp. 61-83, Butterworths Publishers.
Hopwood et al., 1987, Methods of Enzymology 153:116-166.
Heidecker and Messing, 1983, Nucleic Acids Research 11(4):4891-4906.
Zoller and Smith, 1982, Nucleic Acids Research 10(20):6487-6500.
Sanger et al., 1980, J. Mol. Biol. 143:161-178.
Hu and Messing, 1982, Gene 17:271-277.
Ruud et al., 1987, Methods in Enzymology 153:12-34.
Slocombe et al., 1982, PNAS 79:5455-5459.
Kieser et al., 1982, Mol. Gen. Genet. 185:223-238.
Bibb and Hopwood, 1981, J.Gen. Microbiol. 126:427-442.
Pigac et al., 1988, Plasmid 19:222≧230.
Engel and Ullah, 1988, Prep. Biochem. 18(2):137-152.

METHODS FOR TRANSFORMING STREPTOMYCES AND OTHER ACTINOMYCETES

This application is a continuation of application Ser. No. 07/229,943, filed on Aug. 8, 1988, now abandoned.

BACKGROUND OF INVENTION

The application of recombinant DNA technology to industrially important organisms such as Streptomyces and related actinomycete genera requires efficient gene-cloning and transformation procedures. Polyethylene glycol (PEG) induced plasmid transformation of protoplasts has allowed for the development of gene cloning procedures for several species of Streptomyces and related genera. Thus, Acebal et al, 1986, FEMS Microbiol. Lett. 35: 79–82, describe a method for transforming *S. wadayamensis*, a β-lactam antibiotic producer; Bibb et al., 1978, Nature 274: 398–400 describe high frequency transformation of plasmid DNA into Streptomyces; Lampel and Strohl, 1986, Appl. Environ. Microbiol. 51: 126–131, describe transformation and transfection of anthracycline-producing streptomycetes; Matsushima and Baltz, 1985, J. Bacteriol. 163: 180–185, describe efficient plasmid transformation of *S. ambofaciens* and *S. fradiae*; Yamamoto et al., 1986 J. Antibiot. 39: 1304–1313 describe transformation of *S. erythraeus*; Pidcock et al., 1985, Appl. Environ. Microbiol. 50: 693–695, describe transformation of *Thermomonospora fusca* protoplasts; and Matsushima et al., 1987, J. Bacteriol. 169:2298–2300, describe transformation of *Amycolatopsis* (*Nocardia*) *orientalis*. Thus, transformation of various species and strains of Streptomyces and other actinomycetes has been achieved, but in many cases at relatively low frequencies of transformation. Low frequencies of transformation may be due to a multiplicity of reasons, including inefficient uptake of DNA, restriction enzyme digestion of DNA after uptake or difficulties in preparing and/or regenerating protoplasts.

Several difficulties associated with the above-referenced protoplast transformation methods using double-stranded plasmid DNA has, however, impeded the wide application of recombinant DNA technology in many species of Streptomyces and related genera. Most streptomycetes produce a multiplicity of restriction enzymes (see Cox and Baltz, 1984, J. Bacteriol. 159: 499–504; Lomovskaya et al., 1980, Microbiol. Rev. 44: 206–229; McHenney and Baltz, 1988, J. Bacteriol. 170:2276–2282; and Engel, 1987, Appl. and Environ. Microbiol. 53:1-3) that can dramatically decrease the efficiency of plasmid transformation and phage infection. See Matsushima and Baltz, 1985, J. Bacteriol. 163: 180–185; Chater and Wilde, 1980, J. Gen. Microbiol. 116: 323–334; Chater and Wilde, 1976, J. Bacteriol. 128: 644–688; and Chater and Carter, 1978, J. Gen. Microbiol. 109: 181–185. The problem caused by restriction enzymes is often compounded by the rigid procedural requirements for efficient uptake of plasmid DNA and protoplast regeneration. Physiological conditions for cell growth that might minimize the expression of restriction enzymes often inhibit efficient uptake of DNA, plasmid replication and protoplast regeneration.

Several approaches attempting to solve these difficulties have been described. One approach is the use of a phage transduction system for gene cloning and transfer to partially overcome restriction as described in U.S. patent application Ser. No. 07/020,807 (attorney docket no. X-7088) filed Mar. 2, 1987. In a transduction system, the transducing DNA can be packaged into phage particles, which can attach and inject DNA, and thus transduce intact cells, avoiding the use of protoplasts. Intact cells may tolerate a broader range of culture conditions, especially temperature of incubation, better than protoplasts. Since many host restriction systems become less active as the temperature of incubation varies from the temperature of optimal growth, a transduction system using intact cells and varying the temperature of incubation may help to reduce the effectiveness of host restriction enzymes. In addition, raising the multiplicity of infection (m.o.i.), and thus increasing the amount of transducing DNA introduced into a cell, may be used in an attempt to overwhelm host restriction systems. However, a limitation of this system is that only those host cells which are susceptible to infection by such phage may be effectively transduced. In the transduction system of U.S. patent application Ser. No. 07/020,807 a segment of bacterophage FP43 DNA, designated hft for high frequency transduction, was cloned into plasmid pIJ702. The resulting plasmid pRHB101 could be efficiently packaged into FP43 phage heads as linear concatemers to form effective transducing particles.

Another approach to the problem of restriction that was used by Matsushima et al., 1987, Mol. Gen. Genet. 206:393–400 is the development of transformable mutants of *Streptomyces fradiae* defective in several restriction systems. *Streptomyces fradiae* is an important industrial microorganism used to produce the macrolide antibiotic tylosin. In the process of developing *S. fradiae* as a host for gene cloning, Cox and Baltz, 1984, J. Bacteriol. 159:499–504, and Matsushima and Baltz, 1985, J. Bacteriol. 163:180–185, observed that *S. fradiae* expresses potent restriction systems for bacteriophage DNA and plasmid DNA, respectively. Other industrially important species of Streptomyces have been found to be similarly highly restricting. Therefore, to efficiently clone DNA from heterologous sources into such a highly restricting strain as *S. fradiae*, mutants were developed by Matsushima and Baltz, 1987, Mol. Gen. Genet. 206:313–400, lacking one or more restriction enzyme systems. A major problem with this approach is that such mutants must be developed on a strain-by-strain basis and the development and selection of such mutants is not trivial and very time consuming, requiring multiple selection steps. For example, Matsushima et al., 1987, Mol. Gen. Genet. 206: 392–400, describe four initial rounds of mutagenesis accounting for four discrete increases in transformation efficiency with the loss of one modification system, a fifth round of mutagenesis causing the loss of three modification (and presumably restriction) systems, and a final round of mutagenesis causing a large increase in transformation efficiency. This suggests that wild-type *S. fradiae* strains may express greater than five functional restriction systems.

In one aspect, the present invention comprises novel single-stranded DNA vectors and methods of transformation with such vectors that may act to bypass host cell restriction systems and thus permit the efficient transfer of DNA between various species of Streptomyces and between strains of *E. coli* and Streptomyces. These vectors may also be packaged into phage particles, and fused with the cell membrane to permit DNA transfer. These cloning vectors are bifunctional, containing both a Streptomyces origin of replication (for example, SCP2*-ori or pIJ101-ori) and an *E. coli* origin of replication. The present invention thus allows efficient gene transfer between many species of Streptomyces or several other genera of actinomycetes, and *E. coli*.

A number of single-stranded DNA vectors have been described. These vectors are summarized in Table 1.

TABLE 1

| Vectors | Reference or Commercial Source |
|---|---|
| pEMBL series | Dente, et al., 1983, Nucl. Acids Res. 11:1645–55. |
| pBluescript, pBluescribe | Stratagene, 11099 North Torrey Pines Road, La Jolla, CA 92037 |
| fBB101, fBB103 | Barany, 1982, Microbiology 51:125–129. |
| pTZ18, pTZ19 | Mead et al., 1986, Protein Engineering 1:67–74; also available as pTZ18R and pTZ19R from Pharmacia, Molecular Biology Division, Piscataway, N.J. 08854 |
| pKUN9, pKUN19 | Konings et al., 1987, Methods in Enzymology 153:12–34; European Patent Application 86201252.3 |
| pGBT518, pGBT519, pGBTT13 | Gold Biotechnology, 5050 Oakland Avenue, St. Louis, Missouri 63110 |
| pYK331, pYK332, pYK333, pYK335, pYK336 | European Patent Application 84112724.4 |

The single-stranded vectors listed in Table 1 were constructed for the following uses: cloning and dideoxy DNA sequencing (Sanger et al., 1980, J. Mol. Biol. 143: 161–178); site-directed mutagenesis (Zoller and Smith, 1982, Nucl. Acids Res. 10:6487–6500); S1-mapping (Ciliberto et al., 1983 Gene 2:95–113); mRNA cloning (Heidecker and Messing, 1983, Nucl. Acids Res. 11:4891–4906); expression of cloned DNA in *E. coli* (Slocombe et al., 1982, Proc. Natl. Acad. Sci. U.S.A. 79: 5455–5459); production of single-stranded hybridization probes (Hu and Messing, 1982, Gene 17;271–277); heteroduplex analysis and in vitro transcription RNA (Mead et al., 1986, Protein Engineering 1:67–74). None of the single-stranded vectors of Table 1 have been used or suggested for use in transformation of Streptomyces, other actinomycetes, and/or *E. coli*. The fBB101 and fBB103 vectors described by Barany, 1982, Microbiology 51: 125–129, were used in transformation experiments with *Streptococcus pneumoniae*. However, when the transformation efficiencies of single-stranded DNA and double-stranded DNA of the fBB101 or fBB103 vectors were compared, the single-stranded DNA transformed *Streptococcus pneumoniae* at efficiencies 50–100 fold lower than those obtained using double-stranded DNA. Thus, the results of Barany with fBB101 and fBB103 suggest that a single-stranded DNA vector may not be as useful as a double-stranded DNA vector in transformation.

In contrast to these previously described single-stranded vectors and their uses, the vectors of the present invention represent novel hybrids among a Streptomyces plasmid vector, an *E. coli* plasmid vector, and an *E. coli* bacteriophage. These vectors are bifunctional for Streptomyces and *E. coli* because they contain both a Streptomyces and *E. coli* origin of replication. Finally, the single-stranded vectors of the present invention are useful in a method of transformation because they appear to bypass Streptomyces host cell restriction systems and thus permit the efficient transfer of DNA into highly restricting strains of Streptomyces and other organisms that are not able to be transformed at useful frequencies by other methods. These single-stranded vectors are able to transform Streptomyces at frequencies higher than, or at least comparable to, those frequencies obtained using double-stranded DNA.

SUMMARY OF INVENTION

The present invention provides novel vectors and methods for a single-stranded DNA mediated gene transfer system, via transformation or transduction, not only for Streptomyces but also for other organisms throughout the Actimomycetales family, including, but not limited to, Streptosporangium, Actinoplanes, Nocardia, Amycolatopsis, Saccharopolyspora, Arthrobacter, Chainia, Streptoverticillium, Microbispora, Micrococcus, Microtetraspora, Corynebacterium, Actinomadura and Micromonospora, as well as *E. coli*. This single-stranded DNA-mediated gene transfer system appears to bypass host cell restriction systems and thus allows efficient gene transfer.

The present invention provides cloning vectors for use in Streptomyces and other host cells. The development and exploitation of recombinant DNA technology in Streptomyces and other antibiotic-producing organisms, including other actinomycetes, depends upon the availability of suitable cloning vectors. This development has been somewhat retarded by the very small number of vectors presently available that may be able to bypass restriction systems in Streptomyces and other antibiotic-producing organisms and thus transform organisms at useful frequencies. The present invention is useful and especially important because it demonstrates for the first time, the ability of a single-stranded plasmid or phasmid vector to apparently avoid a multiplicity of host cell restriction systems and thus increase the efficiency of gene-transfer into highly restrictive host cell systems, including highly restricting strains of Streptomyces. The present invention greatly expands the number of vectors and hosts suitable for such gene transfer.

The vectors of the present invention are particularly useful because the vectors are small, versatile, and can be transformed and selected in many Streptomyces species and many other heretofore untransformable organisms. Streptomyces provides over half of the clinically important antibiotics and thus is a commercially significant group. The present invention provides new and useful cloning systems and vectors for this industrially important group and allows for the cloning of genes both for increasing the yields of known antibiotics and also for producing new antibiotics, antibiotic derivatives, or any other useful gene product, including a variety of mammalian protein products.

For purposes of the present invention, as disclosed and claimed herein, the following terms are defined below.

Antibiotic—a substance produced by a microorganism which, either naturally or with limited modification, will inhibit the growth of or kill another microorganism or eukaryotic cell.

Antibiotic Biosynthetic Gene—a DNA segment that encodes an enzymatic or other activity that is necessary in the process of converting primary metabolites into antibiotics.

Antibiotic Biosynthetic Pathway—the entire set of antibiotic biosynthetic genes necessary for the process of converting primary metabolites into antibiotics.

Antibiotic Resistance-Conferring Gene—a DNA segment that encodes an enzymatic or other activity that confers resistance to an antibiotic.

AmR—the apramycin-resistant phenotype or gene conferring same.

ApR—the ampicillin-resistant phenotype or gene conferring same.

cos—a specific phage cohesive end sequence that is cut during packaging of the phage DNA.

cosmid—a plasmid in which phage λ cos sites have been inserted, allowing in vitro packaging of the plasmid DNA in phage capsids.

Genetic Library or Genomic Library—a set of recombinant DNA cloning vectors into which segments of DNA, comprising substantially all of the DNA of a particular organism or phage, have been cloned.

hft—high frequency transduction, also used to denote a segment of phage DNA that confers high frequency transducibility to a vector.

Infection—the process of phage replication, wherein the phage attaches to and injects its DNA into the host cell, which then supports phage replication and maturation and ultimately release of phage particles through lysis.

ori—a plasmid origin of replication.

phage—a bacterial virus, also referred to as bacteriophage.

phasmid—a recombinant DNA vector that may act as a phage, or as a plasmid.

plasmid—an autonomous self-replicating extrachromosomal circular DNA.

Recombinant DNA Cloning Vector—any autonomously replicating or integrating agent, including, but not limited to, plasmids, comprising a DNA molecule to which one or more additional DNA segments can be or have been added.

replicon—a unit of genome in which DNA is replicated, and contains an origin for initiation of replication.

Restriction Fragment—any linear DNA molecule generated by the action of one or more restriction enzymes.

Selectable Marker—a segment of DNA incorporated into a recombinant DNA vector, whether freely replicating or integrated, that allows for the identification of cells containing the vector. Selectable markers include antibiotic resistance-conferring genes and other genes such as the β-galactosidase gene.

Sensitive Host Cell—a host cell that cannot grow in the presence of a given antibiotic without a DNA segment that provides resistance thereto.

Shuttle vector—a plasmid constructed to have origins for replication for two hosts (for example, E. coli and Streptomyces), so that it can be used to carry a foreign sequence in either host.

Transduction—the phage-mediated introduction of DNA into a recipient host cell that changes the genotype and results in a change in the recipient cell.

Transductant—a recipient host cell that has undergone transduction.

Transfectant—a recipient host cell that has undergone transformation by phage DNA.

Transformant—a recipient host cell that has undergone transformation by plasmid or phasmid DNA.

Transformation—the introduction of DNA into a recipient host cell that changes the genotype and results in a change in the recipient cell.

tsrR—the thiostrepton-resistant phenotype or gene conferring same.

BRIEF DESCRIPTION OF THE FIGURES

FIG. 3 is a restriction site and function map of cosmid pKC462a.

DETAILED DESCRIPTION OF THE INVENTION

The present invention comprises recombinant DNA phasmid shuttle vectors comprising:

a) a replicon that is functional in E. coli,
b) a replicon that is functional in Streptomyces,
c) a DNA segment that contains a replication origin and morphogenetic signal of a filamentous bacteriophage of E. coli having F pili, and
d) one or more DNA segments that convey resistance to at least one antibiotic when transformed into a sensitive host cell.

The invention further comprises transformants of the aforementioned vectors.

Vectors of the present invention represent novel hybrids among a Streptomyces vector, an E. coli vector, and an E. coli bacteriophage. For example, phasmid vector pOJ401 or pOJ402 can replicate autonomously in Streptomyces and in E. coli since each phasmid vector contains replicons from both organisms. In addition, a bifunctional marker is present for both organisms (for example, AmR in both E. coli and Streptomyces) providing a convenient means to select transformants. Furthermore, the bacteriophage f1 replication origin and morphogenetic signal allow the new vector to be packaged in vitro as single-stranded DNA. The recombinant phasmids can then be used to transform or transfect Streptomyces host cells.

Phasmid shuttle vector pOJ401 is approximately 7 kb and contains a polylinker derived from plasmid pBluescript (available from Stratagene as catalog no. 212201) having a multiplicity of restriction sites which are particularly advantageous for molecular cloning. The starting materials for the construction of phasmid pOJ401 may be obtained as follows. Plasmid pOJ160 can be conventionally isolated from E. coli K12 JM109/pOJ160, a constructed strain deposited and made part of the stock culture collection of the Northern Regional Research Laboratory, Peoria, Ill. 61604. It is available to the public as a source and stock reservoir of the plasmid under the accession number NRRL B-

Figure 1:
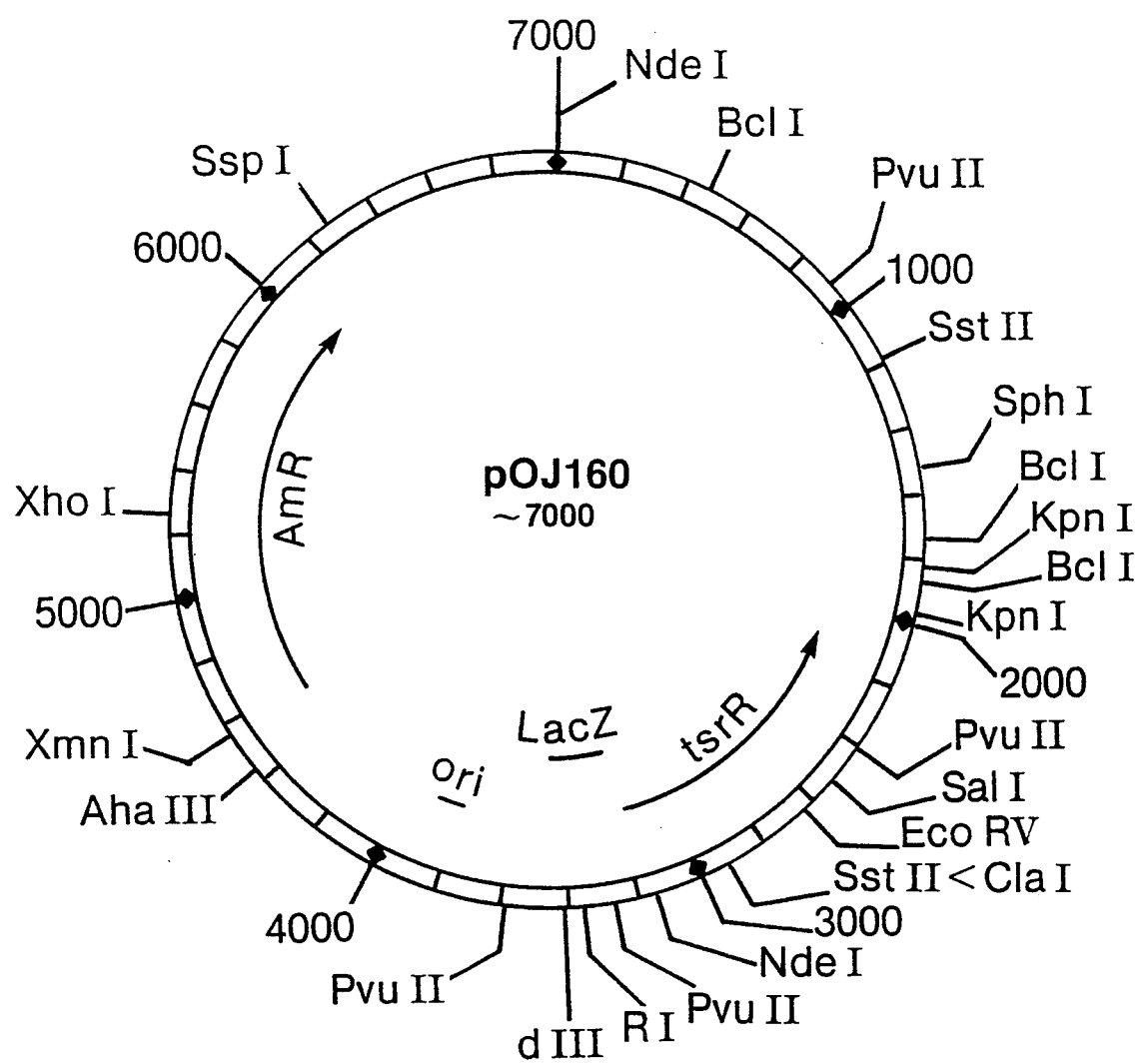
FIG. 1 is a restriction site and function map of plasmid pOJ160.

18088. A restriction site and functional map of plasmid pOJ160 is presented in FIG. 1 of the accompanying drawings. For purposes of the present application, FIG. 1 and all subsequent figures are not drawn to scale. An f1 origin and morphogenetic signal, along with a lacZ gene and a polylinker may be derived from bacteriophage M13 mp19 (available from International Biotechnologies, Inc. (IBI), P.O. Box 9558, 275 Winchester Ave., New Haven, Conn. 06535 as catalog no. 33630) or phagemids pTZ18 and pTZ19 (Mead et al., 1986, Protein Engineering 1:67–74) or phagemid pBluescript (Stratagene).

For convenience and ease of construction, the ~2.25 kb AhaIII-fragment from pBluescript SK+ was ligated to the ~4.5 kb XmnI/SalI (Klenow) fragment of plasmid pOJ160 to yield phasmid pOJ401. Strains of E. coli have been transformed with phasmid pOJ401 DNA, including E. coli K12 XL-1 Blue, E. coli K12 JM109 and other E. coli K12 derivatives such as those listed in Table I of Yanisch-Perron, et al., supra.

Phasmid pOJ401, for example, useful directly as a cloning vector for Streptomyces, other actinomycetes and E. coli, can also be used to construct derivative vectors within the scope of the present invention. Various phasmid pOJ401 restriction sites, including sites in the polylinker, can be used for the insertion of DNA segments provided that the replicons, selectable markers and other necessary plasmid functions are not disrupted. Those skilled in the art understand or can readily determine which sites are advantageous for the ligation or insertion of a particular DNA segment. Phasmid pOJ401 can be restricted and ligated to one or more antibiotic resistance conferring DNA fragments (see, for example, Example 16, where a DNA fragment encoding picromycin resistance was ligated in pOJ401) or to genes for known antibiotics, new antibiotics, antibiotic derivatives or genes for any other useful substance, including mammalian proteins.

The present vectors are not limited to the use of a specific selectable marker. Examples of selectable markers of possible utility include: amikacin, apramycin, chloramphenicol, colistin, dibekacin, erythromycin, gentamicin, hygromycin, kanamycin, neomycin, paromomycin, polymixin B, ribostamycin, rifampicin, spectinomycin, tetracycline, thiostrepton (sulfomycin), tuberactinomycin, and viomycin (capreomycin).

The present vectors also are not limited to the use of a specific replicon from an E. coli or Streptomyces plasmid. Although the E. coli functional replicon exemplified in the present phasmid vectors is derived from plasmid pBR322, other E. coli replicon containing fragments can be obtained from, for example, plasmid pBR324 (disclosed in Bolivar, et al., 1978, Gene 4:121), pBR325 (disclosed in Soberon, et al., 1980, Gene 9:287), or the like, to produce novel bifunctional phasmids.

Additionally, the above-described vectors comprise the Streptomyces replicon SCP2* derived from plasmid SCP2* (Bibb & Hopwood, 1981, J. Gen. Microbiol. 126:427–442) or the Streptomyces replicon pIJ702 derived from plasmid pIJ101 (Kieser et al., 1982, Mol. Gen. Genet. 185:223–238), a variety of known Streptomyces replicons can be used to construct similar vectors. Table 2 is an illustrative, but not comprehensive, listing of Streptomyces plasmids from which additional functional Streptomyces replicons can be obtained. Hopwood et al., 1987, Meth. in Enzym. 153:116–166. Those skilled in the art recognize that all or part of the plasmids may be used to construct vectors exemplifying the present invention so long as the replicon function is not disrupted. The strain of origin of the parent replicon is also listed in Table 2.

TABLE 2

| Streptomyces Plasmids | |
|---|---|
| Plasmid | Strain of Origin (Parent Replicon) |
| SCP2 | Streptomyces coelicolor A3(2) |
| pVE1 | Streptomyces venezuelae ATCC 14585 |
| pJVI | Streptomyces phaechromogenes NRLL-3559 |
| pUC17 | Streptomyces violaceusruber |
| SLP1 | Streptomyces lividans |
| SLP1.2 | Streptomyces lividans 66$^{PP}$ |
| pBT1 | Streptomyces griseobrunneus IPS55066 |
| pSVH1 | Streptomyces venezuelae DSM40755 |
| pFJ103 | Streptomyces granuloruber A39912.13 |
| pTA4001 | Streptomyces lavendulae 1080 |
| pSRC1-6 | Streptomyces roseochromogenes S264 |
| pSL1 | Streptomyces lavendulae KCC SO985 |
| pMG200 | Streptomyces chrysomallus Z1MET 43686 |
| pSF765 | Streptomyces fradiae SF765 |
| pSK2 | Streptomyces kasugaensis MB273 |
| pSG2 | Streptomyces ghangensis DSM 2932 |
| pSG5 | Streptomyces ghangensis DSM 2932 |
| pNM100 | Streptomyces virginiae |

The recombinant DNA phasmid shuttle vectors of the present invention are not limited for use in a single species or strain of Streptomyces or other actinomycetes. To the contrary, the vectors are broadly applicable and can be transformed into host cells of many actinomycetes, either restricting or nonrestricting strains of economically important taxa that produce antibiotics such as aminocyclitol, ansamycin, anthracycline and quinone, macrolide, lincosamide and streptogramin, β-lactam, polyether, and peptide antibiotics or other commercially important products.

Preferred host cells of strains of Strepomyces taxa that produce aminocyclitol antibiotics, and in which the present method is especially useful and the present vectors can be transformed, include cells of, for example: S. kanamyceticus (kanamycins), S. chrestomyceticus (aminosidine), S. griseoflavus (antibiotic MA 1267), S. microsporeus (antibiotic SF-767), S. ribosidificus (antibiotic SF733), S. flavopersicus (spectinomycin), S. spectabilis (spectinomycin), S. rimosus forma paromomycinus (paromomycins, catenulin), S. fradiae var. italicus (aminosidine), S. bluensis var. bluensis (bluensomycin), S. catenulae (catenulin), S. olivoreticuli var. cellulophilus (destomycin A), S. lavendulae (neomycin), S. albogriseolus (neomycins), S. albus var. metamycinus (metamycin), S. hygroscopicus var. sagamiensis (spectinomycin), S. bikiniensis (streptomycin), S. griseus (streptomycin), S. erythrochromogenes var. narutoensis (streptomycin), S. poolensis (streptomycin), S. galbus (streptomycin), S. rameus (streptomycin), S. olivaceus (streptomycin), S. mashuensis (streptomycin), S. hygroscopicus var. limoneus (validamycins), S. rimofaciens (destomycin A), S. hygroscopicus forma glebosus (glebomycin), S. fradiae (hybrimycins, neomycins), S. eurocidicus (antibiotic A16316-C), S. aguacanus (N-methyl hygromycin B), S. crystallinus (hygromycin A), S. noboritoensis (hygromycin), S. hygroscopicus (hygromycins, leucanicidin and hygrolidin), S. atrofaciens (hygromycin), S. kasugaspinus (kasugamycins), S. kasugaensis (kasugamycins), S. netropsis (antibiotic LL-AM31), S. lividus (lividomycins), S. hofuensis (seldomycin complex) and S. canus (ribosyl paromamine). Actinomycetes (other than Streptomyces) and other organisms producing these antibiotics and useful in the present invention, include cells of, for example: Bacillus of various species (various aminoglycosides), Micromonospora of various species (gentamycins), Saccharopolyspora of various species (various aminoglycosides), and *Streptoverticillium flavopersicus* (spectinomycin).

Preferred host cells of strains of Streptomyces taxa that produce ansamycin antibiotics, and in which the present method is especially useful and the present vectors can be transformed, include cells of, for example: *S. collinus* (ansatrienes, napthomycins), *S. diastochromogenes* (ansatrienes, napthomycins), *S. galbus* subsp. *S. griseosporeus* (napthomycin B), *S. hygroscopicus* (herbimycin) *S. hygroscopicus* var. geldanus var. nova (geldamycin), *S. nigellus* (21-hydroxy-25-demethyl 25-methylthioprotostreptovaricin), *S. rishiriensis* (mycotrienes), Streptomyces sp. E/784 (actamycin, mycotrienes), Streptomyces sp. E88 (mycotrienes), *S. spectabilis* (streptovaricins) *S. tolypophorous* (tolypomycin). Actinomycetes (other than Streptomyces) and other organisms producing these antibiotics and useful in the present invention, include cells of, for example: Micromonospora of various species (various ansamycins) and *Nocardia mediterranei* (rifamycin).

Preferred host cells of strains of Streptomyces taxa that produce anthracycline and quinone antibiotics, and in which the present method is especially useful and the present vectors can be transformed, include cells of, for example: *S. caespitosus* (mitomycins A, B, and C), *S. coelicolor* (actinorhodin), *S. coeruleorubidicus* (daunomycin), *S. cyaneus* (ditrisarubicin), *S. flavogriseus* (cyanocycline A), *S. galilaeus* (aclacinomycin A, auramycins, and sulfurmycins), *S. lusitanus* (napthyridinomycin), *S. peuceticus* (daunomycin and adriamycin), and *S. violochromogenes* (arugomycin).

Preferred host cells of strains of Streptomyces taxa that produce macrolide, lincosamide and streptogramin antibiotics, and in which the present method is especially useful, include cells of, for example: *S. caelestis* (antibiotic M188, celesticetin), *S. platensis* (platenomycin), *S. rochei* var. volubilis (antibiotic T2636), *S. venezuelae* (methymycins), *S. griseofuscus* (bundlin), *S. narbonensis* (josamycin, narbomycin), *S. fungicidicus* (antibiotic NA-181), *S. griseofaciens* (antibiotic PA133A, B), *S. roseocitreus* (albocycline), *S. bruneogriseus* (albocycline), *S. roseochromogenes* (albocycline), *S. cinerochromogene* (cineromycin B), *S. albus* (albomycetin), *S. felleus* (argomycin, picromycin), *S. rochei* (lankacidin, borrelidin), *S. violaceoniger* (lankacidins, lankamycin), *S. griseus* (borrelidin), *S. maizeus* (ingramycin), *S. albus* var. coilmyceticus (coleimycin), *S. mycarofaciens* (acetyl-leukomycin, espinomycin), *S. hygroscopicus*, (tylosin), *S. griseospiralis* (relomycin), *S. lavendulae* (aldgamycin), *S. rimosus* (tylosin, neutramycin), *S. deltae* (deltamycins), *S. fungicidicus* var. espinomyceticus (espinomycins), *S. furdicidicus* (mydecamycin), *S. ambofaciens* (spiramycin, foromacidin D), *S. eurocidicus* (methymycin), *S. griseolus* (griseomycin), *S. flavochromogenes* (amaromycin, shincomycins), *S. fimbriatus* (amaromycin), *S. fasciculus* (amaromycin), *S. erythreus* (erythromycins), *S. antibioticus* (oleandomycin), *S. olivochromogenes* (oleandomycin), *S. spinichromogenes* var. suragaoensis (kujimycins), *S. kitasatoensis* (leucomycin A₃ and josamycin), *S. narbonensis* var. josamyceticus (leucomycin A3, josamycin), *S. albogriseolus* (mikonomycin), *S. bikiniensis* (chalcomycin), *S. cirratus* (cirramycin), *S. djakartensis* (niddamycin), *S. eurythermus* (angolamycin), *S. fradiae* (tylosin, lactenocin, macrocin), *S. goshikiensis* (bandamycin), *S. griseoflavus* (acumycin), *S. halstedii* (carbomycin), *S. tendae* (carbomycin), *S. macrosporeus* (carbomycin), *S. thermotolerans* (carbomycin) and *S. albireticuli* (carbomycin). Actinomycetes (other than Streptomyces) and other organisms producing these antibiotics and useful in the present invention, include cells of, for example, *Micromonospora rosaria* (rosaramicin).

Preferred host cells of strains of Streptomyces taxa that produce β-lactam antibiotics, and in which the present method is especially useful and the present vectors can be transformed, include cells of, for example: *S. lipmanii* (penicillin N, 7-methoxycephalosporin C, A16884, MM 4550, and MM 13902), *S. clavuligerus* (PA-32413I, cephamycin C, A16886B, clavulanic acid, other clavams), *S. griseus* (cephamycin A, B), *S. hygroscopicus* (deacetoxycephalosporin C), *S. wadayamensis* (WS-3442-D0, *S. chartreusis* (SF 1623, cephamycin A and B), *S. heteromorphus* and *S. panayensis* (C2081X, cephamycin A and B); *S. cinnamonensis, S. fimbriatus, S. halstedi, S. rochei* and *S. viridochromogenes* (cephamycins A, B); *S. cattleya* (thienamycin); *S. flavovirens, S. flayus, S. fulvoviridis,* and *S. sioyaensis* (MM 4550 and MM 13902); *S. argenteolus* (asparenomycin A, MM 4550 and MM 13902); and *S. olivaceus* (epithienamycin F (MM 1780), MM 4450, and MM 13902). Actinomycetes (other than Streptomyces) and other organisms producing these antibiotics and useful in the present invention, include cells of, for example: Cephalosporium of various species (various β-lactams), *Nocardia lactamadurans* (cephamycin C) and Penicillium of various species (various β-lactams).

Preferred host cells of strains of Streptomyces taxa or other actinomycetes that produce nucleoside antibiotics, and in which the present method is especially useful and the present vectors can be transformed, include cells of, for example: Corynebacterium michiganese pv. rathayi (tunicamycin analogues), Nocardia candidus (pyrazofurin), *S. antibioticus* (ara-A), *S. chartreusis* (tunicamycin), *S. griseoflavus* var. thuringiensis (streptoviridans), *S. griseolus* (sinefungin), and *S. lysosuperificus* (tunicamycin).

Preferred host cells of strains of Streptomyces taxa that produce polyether antibiotics, and in which the present method is especially useful and the present vectors can be transformed, include cells of, for example: *S. albus* (A204, A28695A and B, salinomycin), *S. hygroscopicus* (A218, emericid, DE3936, A120A, A28695A and B, etheromycin, dianemycin), *S. griseus* (girsorixin), *S. conglobatus* (ionomycin), *S. eurocidicus* var. asterocidicus (laidlomycin), *S. lasaliensis* (lasalocid), *S. ribosidificus* (lonomycin), *S. cacaoi* var. asoensis (lysocellin), *S. cinnamonensis* (monensin), *S. aureofaciens* (narasin), *S. gallinarius* (RP 30504), *S. longwoodensis* (lysocellin), *S. flaveolus* (CP38936), *S. mutabilis* (S-11743a) and *S. violaceoniger* (nigericin). Actinomycetes (other than Streptomyces) and other organisms producing these antibiotics and useful in the present invention, include cells of, for example, various species of Actinomadura, Dactylosporangium, Nocardia and Streptoverticillium, which produce various polyethers.

Preferred host cells of strains of Streptomyces taxa or related genera such as, for example, Bacillus, Nocardia, Amycolatopsis, and Actinoplanes that produce peptide antibiotics, and in which the present method is especially useful and the present vectors can be transformed, include cells of, for example: *Amycolatopsis orientalis* and *S. haranomachiensis* (vancomycin); *Nocardia candidus* (A-35512, avoparcin), *Nocardia lurida* (ristocetin), *S. antibioticus* (actinomycin), *S. aureus* (thiostrepton), *S.*

*canus* (amphomycin), *S. pristinaespiralis* (pristamycin), *S. roseosporus* (lipopeptides such as A21978C), *S. eburosporeus* (LL-AM 374), *S. virginiae* (A41030), *S. toyocaensis* (A47934), *Actinoplanes missouriensis* (A4696, actaplanin), and *Actinoplanes teichomyceticus* (teichomycin or teichoplanin).

Preferred host cells of strains of Streptomyces taxa that produce other types of antibiotics, and in which the present method is especially useful and the present vectors can be transformed, include cells of, for example: Streptomyces of various species (amino acid analogues, e.g. cycloserine), *S. coelicolor* (cyclopentane ring-containing, e.g. methylenomycin A), *S. erythrochromogenes* (cyclopentane ring-containing, e.g. sarkomycin), *S. violaceoruber* (cyclopentane ring-containing, e.g. methylenomycin A), *S. venezuelae* (nitro-containing, e.g. chloramphenicol), *S. griseus* (polyenes, e.g. candicidin), *S. nodosus* (polyenes, e.g. amphotericin B), *S. noursei* (polyenes, e.g. nystatin), *S. aureofaciens* (tetracyclines, e.g. tetracycline, chlortetracycline, demethyltetracycline, and demethylchlortetracycline) and *S. rimosus* (tetracyclines, e.g. oxytetracycline).

Preferred host cells of other Streptomyces strains in which the present vectors are especially useful and can be transformed include cells of, for example: *S. granuloruber, S. lividans, S. acrimycins, S. glaucescens, S. parvilin, S. vinaceus, S. espinosus,* and *S. azureus.*

In addition to the above listed representative Streptomyces host cells, the present vectors are also useful and can be transformed into cells of strains of other taxa as described above such as, for example: Bacillus, Staphylococcus, and related actinomycetes, for example, Streptosporangium, Actinoplanes, Nocardia, Amycolatopsis, Saccharopolyspora and Micromonospora. Thus, the vectors of the present invention have wide application and are useful and can be transformed into host cells of a variety of organisms.

While all the embodiments of the present invention are useful, some of the present recombinant DNA cloning vectors and transformants are preferred. Accordingly, preferred vectors are phasmids pOJ401, pOJ402 and pOJ405; and preferred transformants are *Streptomyces fradiae*/pOJ401, *Streptomyces fradiae*/pOJ402, *Streptomyces fradiae*/pOJ405, *Streptomyces griseofuscus/*pOJ401, *Streptomyces griseofuscus*/pOJ402, *Streptomyces griseofuscus*/pOJ405, *Streptomyces toyocaensis*/pOJ401, *Streptomyces toyocaensis*/pOJ402, *Streptomyces toyocaensis*/pOJ405, *E. coli* K12 XL1-Blue/pOJ401, *E. coli* K12 XL1-Blue/pOJ402, and *E. coli* K12 XL1-Blue/pOJ405. Moreover, of this preferred group, phasmid pOJ402 and transformant *Streptomyces griseofuscus* (ATCC 23916)/pOJ402 are most preferred.

The recombinant DNA cloning vectors and transformants of the present invention have broad utility and help fill the need for suitable cloning vehicles for use in Streptomyces and related organisms, in particular, to those in which a multiplicity of restriction enzyme systems have heretofore prevented efficient transformation. Moreover, the ability of the present vectors to confer resistance to an antibiotic that is toxic to non-transformed host cells, also provides a functional means for selecting transformants. This is important because of the practical necessity for determining and selecting the particular cells that have acquired vector DNA. Additional DNA segments, that lack functional tests for their presence, can also be inserted in the present vectors and then transformants containing the nonselectable DNA can be isolated by appropriate antibiotic selection. Such non-selectable DNA segments can be inserted at any site, except within regions necessary for plasmid function, maintainance, and replication, and include, but are not limited to, genes that specify antibiotic modification enzymes, antibiotic resistance, antibiotic biosynthesis, and regulatory or structural genes of all types.

The present invention further comprises a novel method for using a plasmid or phasmid vector to bypass one or more restriction systems, the method comprising:

(a) preparing single-stranded DNA of the vector in *E. coli* or other suitable organism; and (b) transforming an actinomycete host cell with the DNA of step (a).

The single-stranded DNA of a vector to be used for transformation may be prepared from double-stranded DNA by conventional methods, or for some vectors may be prepared directly as single-stranded DNA. Since most strains of actinomycetes have a multiplicity of restriction enzyme systems which can destroy foreign double-stranded DNA taken up by the actinomycete host cell upon transformation, this method may be particularly important for the transfer of DNA into certain restricting strains of actinomycetes, including strains of Streptomyces.

The present invention also comprehends a method for selecting a recombinant DNA-containing actinomycete host cell, the method comprising:

1) transforming an antibiotic-sensitive, actinomycete host cell with a recombinant DNA phasmid shuttle vector, the vector comprising a DNA sequence that confers resistance to an antibiotic; and 2) culturing the transformed cell under conditions suitable for selection for antibiotic resistant transformants.

The present invention comprises the vectors and transformants used to practice the aforementioned method.

The present method for selecting actinomycete transformants by their expression of antibiotic resistance is best illustrated by constructing vectors for transformation of assorted actinomycete host cells. One example of such a vector is phasmid pOJ402. The starting materials used in the construction of phasmid pOJ402 are available commercially or have been deposited and made part of the permanent stock culture collection of the Northern Regional Research Laboratory, Agricultural Research Service, 1815 North University Street, U.S. Department of Agriculture, Peoria, Ill. 61604 or the American Type Culture Collection, 12301 Parklawn Drive, Rockville, Md. 20852. The accession numbers of the strains harboring the starting materials used in the construction of phasmid pOJ402 are: 1) ATCC 39155—*Streptomyces lividans*/pIJ702; and 2) NRRL B-15972—*E. coli* K12 SF8/pKC462a. Plasmids pUC19 and pBluescript SK+ are available from Stratagene. The construction protocol for phasmid pOJ402 is described in Example 13. As constructed, phasmid pOJ402 contains an apramycin resistance gene for selection in actinomycetes (including Streptomyces) and *E. coli* and a pIJ101 derived from pIJ702 origin for replication in Streptomyces. These elements may be obtained on an ~4.5 kb XmnI/EcoRI (Klenow) fragment from plasmid pOJ361. These elements may be derived as a variety of fragments from a variety of plasmid vectors which contain one or more of these elements. In particular, other Streptomyces replicons may be used. In addition, phasmid pOJ402 contains an M13 replication origin, an f1 morphogenetic signal, a lacZ gene, a polylinker and an *E. coli* origin for replication in *E. coli*. These additional elements may be obtained on an ~2.2 kb AhaIII fragment from plasmid pBluescript or from a variety of fragments from a variety of plasmid or phage vectors which contain one or more of these elements.

The novel vectors of the present invention comprise a Streptomyces replicon, an *E. coli* replicon, and an apramycin resistance-conferring restriction fragment. Because amplification and manipulation of plasmids is done faster and more efficiently in *E. coli* than in Streptomyces, it is convenient to add DNA sequences encoding an *E. coli* replicon that also allow the vectors to replicate in *E. coli*. Thus, the additions of functional replicon-containing restriction fragments from *E. coli* plasmids such as, for example, pBR322, pACYC184, pBR325, pBR328 and the like are highly advantageous and add to the general utility of vectors exemplifying the present invention.

The vectors for use in the present method confer apramycin resistance to sensitive Streptomyces or related actinomycete host cells, as well as *E. coli*. The apramycin resistance-conferring vectors of the present invention are useful for insuring that linked DNA segments are stably maintained in host cells over many generations. These genes or DNA fragments, covalently linked to the apramycin resistance-conferring fragment and propagated in Streptomyces, are maintained by exposing the transformants to levels of apramycin that are toxic to non-transformed cells. Therefore, transformants that lose the vector, and consequently any covalently linked DNA, cannot grow and are eliminated from the culture. Thus, the vectors of the present invention can stabilize and maintain a DNA sequence of interest.

The methods, cloning vectors and transformants of the present invention provide for the cloning of genes to improve yields of various products that are currently produced in Streptomyces and related cells. Examples of such products include, but are not limited to, streptomycin, tylosin, cephalosporins, actaplanin, narasin, monensin, tobramycin, erythromycin and the like. The present invention also provides selectable vectors that are useful for cloning, characterizing and reconstructing DNA sequences that encode: commercially important proteins such as, for example, human insulin, human proinsulin, glucagon, interferon and the like; enzymatic functions in metabolic pathways leading to commercially important processes and compounds; or for control elements that improve gene expression. These desired DNA sequences also include, but are not limited to, DNA that codes for enzymes that catalyze synthesis of derivatized antibiotics such as, for example, streptomycin, cephalosporin, tylosin, actaplanin, narasin, monensin and erythromycin derivatives, or for enzymes that mediate and increase bioproduction of antibiotics or other products. The capability for inserting and stabilizing such DNA segments thus allows for increasing the yield and availability of antibiotics that are produced by Streptomyces and related actinomycetes.

Actinomycetes, including Streptomyces, can be cultured in a number of ways using any of several different media. Carbohydrate sources which are preferred in a culture medium include, for example, molasses, glucose, dextrin and glycerol. Nitrogen sources include, for example, soy flour, amino acid mixtures and peptones. Nutrient inorganic salts are also incorporated and include the customary salts capable of yielding sodium, potassium, ammonia, calcium, phosphate, chloride, sulfate and like ions. As is necessary for the growth and development of other microorganisms, essential trace elements are also added. Such trace elements are commonly supplied as impurities incidental to the addition of other constitutents of the medium.

Actinomycetes, including Streptomyces, are grown under aerobic culture conditions over a relatively wide pH range of about 5 to 9 at temperatures ranging from about 15° C. to 40° C. For phasmid or plasmid stability and maintenance, it is desirable to start with a culture medium at a pH of about 7.2 and maintain a culture temperature of about 30° C.

The following examples further illustrate and detail the invention disclosed herein. Both an explanation of and the actual procedures for constructing the invention are described where appropriate.

EXAMPLE 1

Culture of *E. coli* K12 JM109/pOJ160 Isolation of Plasmid pOJ160

A. Culture of *E. coli* K12 JM109/pOJ160

A 5 ml culture of *E. coli* K12 JM109/pOJ160 (NRRL B18088) was grown in the presence of 200 μg/ml apramycin in TY media (1% tryprone, 0.5% NaCl and 0.5% yeast extract, pH 7.4) until the cells reached stationary phase.

The 5 ml culture was then used to inoculate a flask containing 250 ml of TY media containing 200 μg/ml apramycin and growth was continued until the cells reached stationary phase.

B. Isolation of Plasmid pOJ160

The culture was centrifuged and the cell pellet resuspended in 7 ml of a sucrose solution (25% w/v sucrose; 50 mM Tris-HCl, pH 8.0; and 1 mM EDTA). Then, 0.4 ml of 0.5M EDTA and 1 ml of a 5 mg/ml lysozyme solution in 0.25M Tris-HCl, pH 8.0 were added to the resuspended cell pellet and the resultant mixture incubated on ice (4° C.) for 15 minutes. After the 15 minute incubation, 0.75 ml of a solution that was 50 mM Tris-HCl, pH 8.0; 6 mM EDTA; and 0.1% Triton X-100 were added to the lysozyme-treated cells and mixed by inversion.

The lysed cell mix was then centrifuged at 20,000 rpm in a Sorvall (DuPont Inst. Products, Biomedical Division, Newton, Conn. 06470) SS34 rotor for 40 minutes until the cell debris formed a loose pellet. The cell debris pellet was discarded and the supernatant was adjusted to 30 ml with TE buffer (50 mM Tris-HCl, pH 8.0; 1 mM EDTA). Then 28.6 g cesium chloride were added, with a resulting density 1.55 g/ml.

Centrifugation in a Beckman (Scientific Instrument Division, Campus Drive at Jamboree Blvd., Irvine, Calif. 92713) Vti 50 rotor (45,000 rpm, 16 hours, 20° C.) using cesium chloride gradients with ethidium bromide, was carried out to purify the plasmid DNA. Following centrifugation, the desired plasmid pOJ160 DNA was collected and the ethidium bromide and cesium chloride removed by extracting 4 times with isopropanol saturated with 20× SSC (0.15M NaCl, 0.015M sodium citrate). The extracted solution was dialyzed against 1000 volumes of TE buffer overnight at room temperature, and then precipitated with ethanol. The approximately 300 μg of plasmid pOJ160 DNA obtained by this procedure was dissolved in 300 μl of TE buffer and stored at −20° C. A restriction site and function map of plasmid pOJ160 is presented in FIG. 1 of the accompanying drawings.

EXAMPLE 2

Culture of *E. coli* K12 JM109/pBluescript SK+ and Isolation of Plasmid pBluescript SK+

A. Culture of *E. coli* K12 JM109/pBluescript SK+

*E. coli* K12 JM109/pBluescript SK+ was grown in substantial accordance with the procedure of Example 1, except that the cells were grown in 100 μg/ml ampicillin as the selective marker, rather than 200 μg/ml apramycin. Plasmid pBluescript SK+ DNA was initially obtained from Stratagene, 11099 North Torrey Pines Road, La Jolla, Calif. 92037 and used to transform *E. coli* K12 JM109 cells (also available from Stratagene or Bethesda Research Laboratories (BRL), P.O. Box 6009, Gaithersburg, Md. 20877) in substantial accordance with the transformation procedure of Example 4.

B. Isolation of Plasmid pBluescript SK+

Plasmid pBluescript SK+ DNA was isolated in substantial accordance with the procedure of Example 1B. The plasmid pBluescript SK+ DNA thus obtained was dissolved in TE buffer, and stored at −20° C. at a concentration of ~1 μg/μl.

EXAMPLE 3

Construction of Phasmid pOJ401

A. AhaIII Digestion of Plasmid pBluescript SK+ DNA

Approximately 3 μg (3 μl) of plasmid pBluescript SK+ isolated in Example 2 were added to 2 μl of 10× AhaIII buffer (1.5M NaCl; 60 mM Tris-HCl, pH 7.5; 60 mM MgCl$_2$; and 10 mM dithiothreitol (DTT)), 1 μl (about 40 units; all enzyme units referred to herein, unless otherwise indicated, refer to the unit definitions of New England Biolabs (NEB), 32 Tozer Road, Beverly, Mass. 01915, although the actual source of enzymes may have been different) of restriction enzyme AhaIII and 14 μl of H$_2$O and, after gentle mixing, reacted at 37° C. for two hours.

After reacting, the digest was extracted once with buffered pH 8.0 phenol and once with chloroform (CHCl$_3$). The sodium acetate concentration was then adjusted to 0.3M, pH 8.0, and two volumes of ethanol added. After mixing, the solution was chilled to −70° C. and the nucleic acid pelleted by centrifugation. The supernatant was discarded and the DNA pellet rinsed once with 70% ethanol and then dried. The AhaIII-digested plasmid pBluescript SK+ was then resuspended in 20 μl of TE buffer.

B. Isolation of the ~4.5 kb Replicon-Containing XmnI-SalI (Klenow) Fragment of Plasmid pOJ160

Approximately 10 μg (10 μl) of the plasmid pOJ160 DNA isolated in Example 1 were added to 10 μl 10× XmnI buffer (500 mM NaCl; 60 mM Tris-HCl, pH 7.5; 60 mM MgCl$_2$; and 10 mM DTT), 2 μl (about 20 units) of restriction enzyme XmnI and 78 μl of H$_2$O and incubated at 37° C. for two hours. Then, 11 μl of 10× SalI buffer (1.5M NaCl; 60 mM Tris-HCl, pH 7.5; 60 mM MgCl$_2$; and 2 mM EDTA) were added and 2 μl (about 20 units) of restriction enzyme sail were added, and incubated at 37° C. for two hours.

Next, 1 μl (about 5 units) of Klenow enzyme was added to the solution and 1 μl of a solution containing each of the 4 dNTPS (at 10 mM each) was added, and the reaction was incubated at 37° C. for 1 hour. The Klenow-treated digest was then electrophoresed on a 1% agarose gel. The desired ~4.5 kb XmnI-SalI (Klenow) fragment of plasmid pOJ160 was then isolated by conventional electrophoretic gel means using DEAE paper (Whatman Laboratory Products Inc., 9 Bridgewell Place, Clifton, N.J. 07014). The fragment was eluted from the DEAE paper by incubation in high salt buffer (1.0M NaCl in TE buffer) at 60° C. for 5 minutes and the paper fragments were pelleted by centrifugation. The supernatant was removed and the DNA precipitated from the supernatant with ethanol. About 5 μg of the fragment are obtained. The purified fragment is suspended in 20 μl of TE buffer.

C. Ligation of AhaIII-Cut Plasmid pBluescript SK+ to the ~4.5 kb XmnI-SalI (Klenow) Restriction Fragment of Plasmid pOJ160

Five μl of the AhaIII-cut plasmid pBluescript SK+ isolated in part A of this Example, were added to 5 μl of the ~4.5 kb XmnI-SalI (Klenow) fragment isolated in part B above, and then 4 μl of 10× T4 DNA ligase buffer (500 mM Tris-HCl, pH 7.4; 100 mM MgCl$_2$; 100 mM DTT; and 10 mM ATP), 1 μl (about 500 units) of T4 DNA ligase and 25 μl of H$_2$O were added to the DNA. After gentle mixing, the reaction mixture was incubated at 16° C. for 16 hours. This reaction produced phasmid pOJ401.

D. Isolation of Phasmid pOJ401

Figure 2:
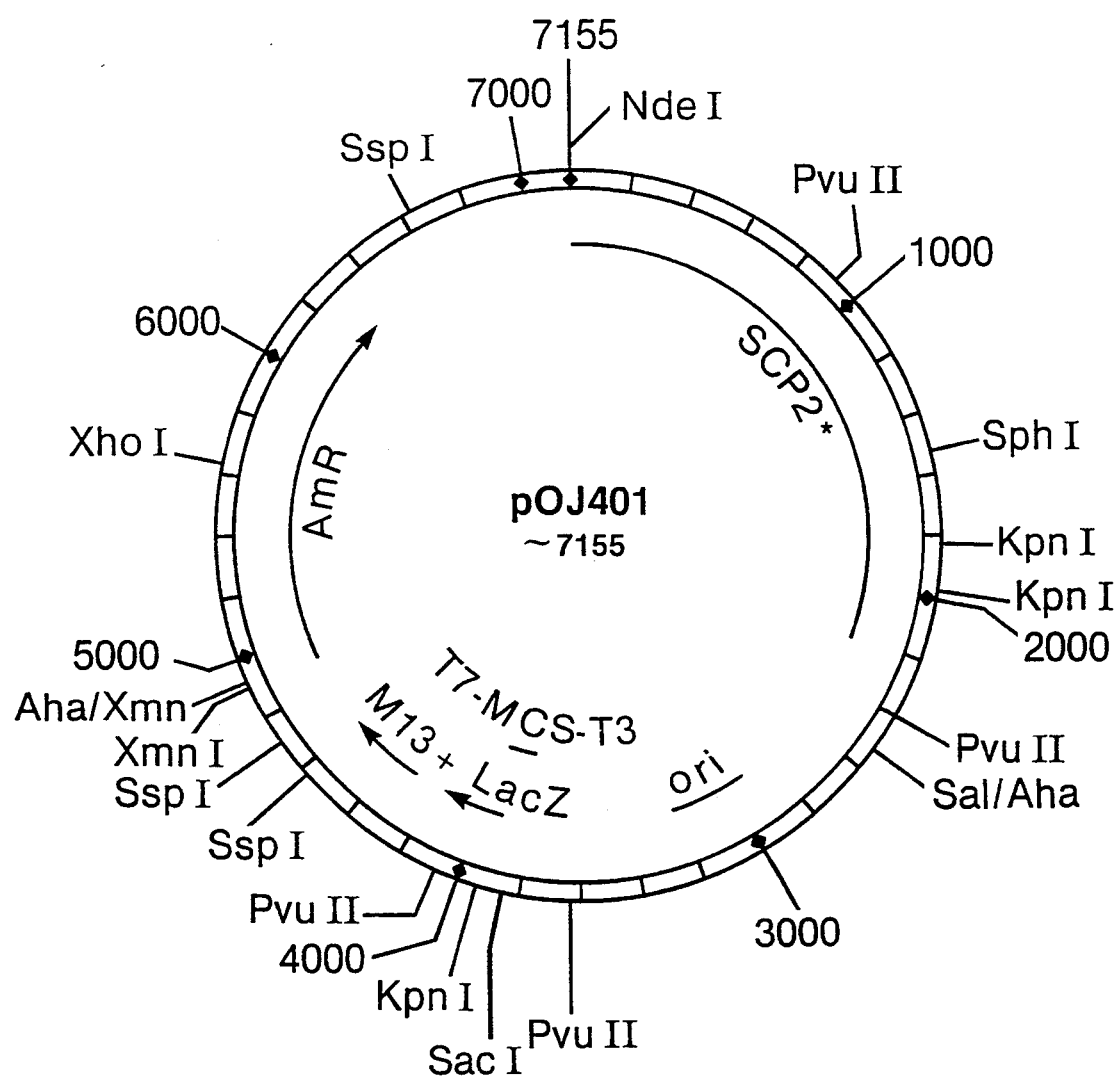
FIG. 2 is a restriction site and function map of phasmid pOJ401.

Phasmid pOJ401 DNA was isolated in substantial accordance with the procedure of Example 1B. The phasmid pOJ401 DNA thus obtained was dissolved in TE buffer, and stored at −20° C. at a concentration of ~1 μg/μl. A restriction site and function map of phasmid pOJ401 is presented in FIG. 2 of the accompanying drawings.

EXAMPLE 4

Transformation of *E. coli* K12 XL1-Blue Cells with Phasmid pOJ401

A. Growth of Cultures for Preparation of Cells for Transformation

*E. coli* K12 XL1-Blue cells (Bullock et al., 1987, BioTechniques 5:376-378; available from Stratagene) were grown in TY broth or on a TY-agar plates. From a plate of TY-agar containing 20 μg/ml tetracycline, a single colony of *E. coli* K12 XL1-Blue cells was picked and used to inoculate 10 ml of TY broth containing 100 μg/ml tetracycline. The 10 ml culture was grown overnight (~16 hours) at 37° C. with shaking. This overnight culture was used to inoculate 100 ml of TY broth containing 10 μg/ml tetracycline in a 500 ml flask. The culture was incubated with vigorous shaking at 37° C. until an O.D.$_{550}$ of 0.5 was reached. Then, the cell culture was incubated on ice for 15 minutes, and, after this incubation, centrifuged at 4° C. for 10 minutes at 10,000 rpm in a Sorvall SS34 rotor. The supernatant was discarded and the cell pellet was gently resuspended in 50 ml of a sterile solution at 4° C. of 10 mM morpholinopropane sulfonic acid (MOPS) at pH 7.0 and 10 mM rubidium chloride (RbCl). The cells were pelleted by centrifugation as described above. The supernatant was discarded and the cell pellet was gently resuspended in 50 ml of a sterile solution of 0.1M MOPS, pH 6.5; 50 mM CaCl$_2$; and 10 mM RbCl. The cell suspension was placed on ice for 15 minutes and then centrifuged as described above. The supernatant was removed and the pellet was gently resuspended in 20 ml of a sterile solution of 0.1M MOPS, pH 6.5, 50 mM CaCl$_2$, 10 mM RbCl and 20% glycerol. The cell suspension was dispensed in 200 μl aliquots and quick frozen at −70° C. The cells are ready for transformation and may be stored frozen and then thawed for the transformation procedure in part B below of this Example.

B. Transformation Procedure

A 200 μl aliquot of *E. coli* K12 XL1-Blue cells, prepared as described in part A above was thawed and 1 μl (about 1 μg) of phasmid pOJ401 DNA prepared in Example 3D was added. The mixture was incubated on ice for 30 minutes. Next, the mixture was heat-shocked by incubating at 42° C. for 2 minutes, followed by incubation on ice for 5 minutes. Then, the cell suspension was microfuged for 30 seconds and the supernatant discarded. The cell pellet was resuspended in 5 ml of TY broth and incubated at 37° C. on a roller drum for 2 hours. Aliquots of approximately 100 μl were plated on TY-agar containing 200 μg/ml apramycin and the inoculated TY-agar plates were incubated overnight at 37° C. to allow transformants to grow. The desired transformants were *E. coli* K12 XL1-Blue/pOJ401 cells. The apramycin-resistant transformants were examined by restriction enzyme analysis to identify the *E. coli* K12 XL1-Blue/pOJ401 transformants. Plasmid DNA was prepared for this analysis by the method of Example 12.

EXAMPLE 5

Preparation of Single-Stranded DNA from *E. coli* K12 XL1-Blue/pOJ401 for Transformation To 100 ml of TY broth in a 500 ml flask was added 1 ml of an overnight culture of *E. coli* K12 XL1-Blue/pOJ401 prepared in substantial accordance with the procedure in Example 4 and grown at 37° C. in TY broth with 200 μg/ml apramycin. Then, 50 μl of VCS-M13 helper phage (~2.0×10$^7$ PFU) (Stratagene). This gave a multiplicity of infection (MOI) of ~0.1. This 100 ml culture was incubated overnight at 37° C. with vigorous shaking. After overnight incubation, the 100 ml cell culture was centrifuged to pellet the cells. Supernatant containing extruded phage was obtained and filtered through a 0.4μ filter.

Fifty μl of 10 mg/ml DNAse I (about 5000 units) (Bethesda Research Laboratories Inc. (BRL) 8717 Grovemont Circle, Gaithersburg, Md. 20877) and 50 μl (about 5 units) of 2 mg/ml RNase A (Boehringer Mannheim Biochemicals, 7941 Castleway Drive, Indianapolis, Ind. 46250) were added to the filtered supernatant, and then incubation was at 37° C. for 2 hours. Following incubation, 75 ml of 20% PEG-8000 (Sigma, P.O. Box 14508, St. Louis, Mo. 63178) and 14.6% NaCl solution were added to the DNAse and RNase treated supernatant, then the solution was mixed well and placed at −80° C. for about 1 hour. After chilling, the phage were precipitated from the solution by centrifugation at 10,000 rpm in a Sorvall GSA rotor for 15 minutes at 4° C. The supernatant was discarded and the phage pellet was resuspended in 800 μl of TE buffer. Then, 200 μl of 1M Tris-HCl, pH 8.0, 200 μl 10.5M EDTA and 10 μl of 20% sodium dodecyl sulfate (SDS) were added to the phage suspension. This mixture was heated for 15 minutes at 70° C., then cooled to room temperature, and 140 μl of 3M sodium acetate were added, with an equal volume of isopropanol at room temperature. The single-stranded plasmid DNA was then precipitated by microfuging the solution for 15 minutes at room temperature. The pellet of single-stranded DNA was resuspended in 100 μl of TE buffer. The O.D.$_{260}$ of the single-stranded DNA solution was determined and ~18 μg of single-stranded DNA were obtained.

EXAMPLE 6

Preparation of Double-Stranded DNA from *E. coli* K12 XL1-Blue/pOJ401 for Transformation

*E. coli* K12 XL1-Blue/pOJ401 cells were grown in substantial accordance with the procedure of Example 1A. The double-stranded phasmid pOJ401 DNA was isolated in substantial accordance with the procedure of Example 1B. The double-stranded phasmid pOJ401 DNA thus obtained was dissolved in TE buffer, and stored at ~20° C. at a concentration of ~1 μg/μl.

EXAMPLE 7

Transformation of *E. coli* K12 JM109 with Single-Stranded and Double-Stranded DNA of Phasmids pOJ401 and pOJ402

*E. coli* K12 JM109 cells (Yanisch-Perron et al., 1985, Gene 33:103–119; available from Stratagene) were grown in substantial accordance with the procedure of Example 4A, except that no tetracycline was added. The cells are made competent for transformation in substantial accordance with the procedure of Example 4A and transformed with either single-stranded or double-stranded phasmid pOJ401 or pOJ402 DNA in substantial accordance with the procedure of Example 4B. The transformants were plated as follows: 100 μl from a 5 ml transformation culture in TY broth were plated on TAXI (TY broth, 200 μg/ml apramycin, 40 μg/ml XGal, and 1 mM IPTG)-agar. The TAXI-agar plates were incubated at 37° C. overnight; the next day, colonies were counted.

Table 3 shows the results of an illustrative experiment. Results are expressed in Table 3 as transformation efficiencies (number of transformants colonies per μg DNA). The results indicate that single-stranded DNA can be used to transform *E. coli* K12 JM109 cells as effectively as double-stranded DNA.

TABLE 3

| Cells/DNA | Strandedness* | Transformation Efficiency |
|---|---|---|
| JM109/pOJ401 | ds | 1.2 × 10$^5$/μg |
|  | ss | 2.3 × 10$^3$/μg** |
| JM109/pOJ402 | ds | 1.1 × 10$^5$/μg |
|  | ss | 1.1 × 10$^5$/μg |

*ds = double-stranded DNA; ss = single stranded DNA
**The single-stranded pOJ401 DNA used for transformation contained ~50–80% contaminating helper phage DNA.

EXAMPLE 8

Transformation of *Streptomyces griseofuscus* with Single-Stranded and Double-Stranded DNA of Phasmids pOJ401 and pOJ402

Frozen cultures (mycelial fragments) of *Streptomyces griseofuscus* (ATCC 23916) were stored in trypticase soy broth (TSB) (Difco Laboratories Inc., P.O. Box 1058A, Detroit, Mich. 48232) at −70° C. A frozen culture of mycelial fragments was thawed and used to inoculate 10 ml of TSB. This initial 10 ml culture was grown overnight at 30° C. The overnight culture was homogenized to break up the mycelial fragments and 0.5 ml of the homogenate was used to inoculate 10 ml of TSB containing 0.4% glycine. This second 10 ml culture was incubated overnight at 30° C. This culture was homogenized and 0.5 ml used to inoculate 10 ml of TSB containing 0.4% glycine, and this third culture was incubated overnight at 30° C. This culture was similarly homogenized and the cells were pelleted in a table top centrifuge at 2,000 rpm for 10 minutes. The pellet was resuspended in 10 ml of P (Protoplast) medium. The P medium (~100 ml) was prepared as follows:

| Ingredient | Amounts |
| --- | --- |
| Sucrose | 10.30 g |
| $K_2SO_4$ | 0.25 g |
| $MgCl_2.6\ H_2O$ | 2.02 g |
| Trace Element Solution (for 1 liter.: 40 mg $ZnCl_2$; 200 mg $FeCl_3.6H_2O$; 10 mg $CuCl_2.2\ H_2O$; 10 mg $MnCl_2.4\ H_2O$; 10 mg $Na_2B_4O_7.10H_2O$; 10 mg $(NH_4)_6Mo_7O_{24}.4\ H_2O$) 0.2 ml | |
| $dH_2O$ to | 80.0 ml |
| After autoclaving add: | |
| $KH_2PO_4$ (0.5%) | 1.0 ml |
| $CaCl_2.2H_2O$ (3.68%) | 10.0 ml |
| (N-tris (hydroxymethyl)-methyl-2-aminoethane sulphonic acid) "TES" buffer, 0.25M, pH 7.2 | |

The cell suspension was centrifuged as above, the supernatant discarded, and the cell pellet resuspended in 10 ml of P medium with 5 mg/ml lysozyme. The lysozyme treated cell suspension was incubated at 30° C. for 1 hour with gentle shaking every 15 minutes to form protoplasts. The protoplasts so formed were pelleted by centrifugation as above and resuspended in 10 ml P medium. This step was repeated and the washed protoplasts were suspended in 3 ml of P medium, ready for transformation.

For the transformation, 3 µl of phasmid pOJ401 or pOJ402 DNA, either single-stranded (Example 5) or double-stranded (Example 6), were added to 150 µl protoplasts and 101 µl of 55% PEG 1000 in P medium. The DNA-protoplast PEG suspension was held at room temperature for 30 seconds before adding this suspension to 4 ml of R2 overlay (R2 medium with 0.41% agar) which was then poured on an R2 agar plate. R2 (Regeneration) medium (~1 liter) was prepared as follows:

| Ingredient | Amount |
| --- | --- |
| Sucrose | 103.00 g |
| $K_2SO_4$ | 0.25 g |
| Trace Element Solution | 2.00 ml |
| $MgCl_2.6H_2O$ | 10.12 g |
| glucose | 10.00 g |
| L-asparagine.$1H_2O$ | 2.00 g |
| casamino acids (Difco) | 0.10 g |
| agar | 22.00 g |
| $dH_2O$ to | 700 ml |
| After autoclaving add: | |
| $KH_2PO_4$ (0.05 g/100 ml) | 100 ml |
| $CaCl_2$ (2.22 g/100 ml) | 100 ml |
| TES buffer (5.73 g/100 ml, pH 7.2 | 100 ml |
| NaOH (5N) | 1 ml |

The R2 agar plate with R2 overlay containing transformed protoplasts was incubated at 30° C. overnight. The next day, 4 ml of a second R2 overlay containing apramycin were poured onto the plate to yield a final plate concentration of 25 µg/ml apramycin. The plate was again incubated at 30° C., for 5 days. At the end of the 5 day incubation, transformant colonies were counted and transformation efficiencies were calculated and are presented in Table 4. The plasmid DNA of the transformants was prepared for restriction enzyme analysis by the miniprep procedure of Example 12. Alternatively, the plasmid DNA was shuttled back into E. coli K12 JM109 (Example 9) for restriction enzyme analysis.

Table 4 shows the results of an illustrative transformation experiment. The results indicate that single-stranded phasmid pOJ401 or pOJ402 DNA transforms S. griseofriscus at high frequencies, and with frequencies comparable to those with double-stranded DNA.

TABLE 4

| Cells/DNA | Strandedness | Transformation Efficiency |
| --- | --- | --- |
| S. griseofuscus/pOJ401 | ds | $>10^5$ |
|  | ss | $-2 \times 10^4$ |
| S. griseofuscus/pOJ402 | ds | $4.6 \times 10^5$ |
|  | ss | $1.8 \times 10^6$ |

EXAMPLE 9

Shuttling of Phasmid pOJ401 or pOJ402 between Streptomyces griseofuscus and Strains of E. coli K12

Phasmid pOJ401 and pOJ402 DNA that was transformed into Streptomyces griseofuscus in substantial accordance with the procedure of Example 8, could be shuttled between Streptomyces griseofuscus and various strains of E. coli K12, including the JM109 and RR1 strains. A single colony plug from the transformation plates obtained according to Example 8 was used to inoculate 5 ml of TSB with 25 µg/ml apramycin. The 5 ml culture was homogenized and then incubated at 30° C. overnight on a roller drum. After the overnight incubation, the culture was homogenized again. The DNA from ~1.5 ml of this culture was prepared in substantial accordance with the procedure of Example 12 and the DNA was resuspended in 20 µl of TE buffer. Five µl of the 20 µl sample was used to transform E. coli K12 JM109 in substantial accordance with the procedure of Example 4. Transformants were selected by growth at 37° C. overnight on TAXI plates. To confirm that phasmid pOJ401 or pOJ402 DNA used to transform was intact after transformation, phasmid DNA was prepared in substantial accordance with the procedure of Example 12 and analyzed by restriction enzyme analysis.

There are several advantages to analyzing the phasmid DNA in E. coli rather than in Streptomyces. First, there is more DNA for analysis (higher copy number in E. coli) and secondly, the minipreps yield cleaner, purer DNA for the restriction enzyme analysis.

EXAMPLE 10

Transformation of Streptomyces fradiae with Single-Stranded and Double-Stranded DNA of Phasmids pOJ401 and pOJ402

Streptomyces fradiae PM77 (Baltz and Seno, 1988, Ann. Rev. Microbiol. volume 39, in press) cells were transformed with single-stranded or double-stranded DNA of phasmid pOJ401 or pOJ402 in substantial accordance with the transformation procedure for Streptomyces griseofuscus in Example 8. Transformant colonies were counted and transformation efficiencies were calculated and are presented in Table 5. The phasmid DNA of the transformants was analyzed as described in Example 8.

Table 5 shows the results of an illustrative transformation experiment. The results indicate that single-stranded pOJ401 or pOJ402 DNA transforms *S. fradiae* PM77 at high frequencies, and with frequencies comparable to, even exceeding, those frequencies with double-stranded DNA. In other experiments using a more restricting strain of *Streptomyces fradiae* (GS62), the results indicated that single-stranded pOJ401 or pOJ402 DNA transforms *S. fradiae* GS62 at frequencies approximately 1000 fold greater than those frequencies with double-stranded DNA.

TABLE 5

| Cells/DNA | Strandedness | Transformation Efficiency |
|---|---|---|
| *S. fradiae* PM77/pOJ401 | ds | $5.4 \times 10^4$ |
| | ss | $1.0 \times 10^7$ |
| *S. fradiae* PM77/pOJ402 | ds | $1.5 \times 10^5$ |
| | ss | $1.8 \times 10^6$ |

EXAMPLE 11

Transformation of *Streptomyces toyocaensis* with Single-Stranded and Double-Stranded DNA of Phasmids pOJ401 and pOJ402

*Streptomyces toyocaensis* 80934 (NRRL 18112) or MJ16 (a non-restricting variant of 80934 prepared by the method of Matshushima, et al., 1987, Mol. Gen. Genet. 206:393–400) cells were transformed with single-stranded or double-stranded DNA of phasmid pOJ401 and pOJ402 in substantial accordance with the transformation procedure of Example 8, except as follows. For the transformation, 1.0 ml of protoplasts were pelleted, the supernatant was decanted and ~5–10 μl of phasmid pOJ401 or pOJ402 DNA, either single-stranded (Example 5) or double-stranded (Example 6), were added to pelleted protoplasts with 0.5 ml of 55% PEG 1000 in P medium.

The DNA-protoplast-PEG suspension was then plated with R2 overlay onto TSB/R2 (120 ml of TSB per liter of R2 medium) agar plates, incubated at 30° C. overnight, and overlaid the next day with R2 overlay containing 5 μg/ml apramycin. The plate was then incubated at 30° C. for 7 days. At the end of the 7 day incubation, transformant colonies were counted and transformation efficiencies calculated, as presented in Table 6. The phasmid DNA of the transformants was analyzed as described in Example 8. Table 6 shows the results of an illustrative transformation experiment. Results are shown for *S. toyocaensis* MJ16 which is a non-restricting variant strain and for *S. toyocaensis* 80934 which has restriction activity.

TABLE 6

| Cells/DNA | Strandedness | Transformation Efficiency |
|---|---|---|
| *S. toyocaensis* MJ16/ pOJ401 | ds | $3.0 \times 10^3$ |
| | ss | $1.8 \times 10^3$ |
| *S. toyocaensis* KJ16/ pOJ402 | ds | $9.0 \times 10^2$ |
| | | $(2.7 \times 10^3)$ |
| | ss | $1.5 \times 10^3$ |
| | | $(9.3 \times 10^2)$ |
| *S. toyocaensis* 80934/ pOJ401 | ds | $1.2 \times 10^1$ |
| | ss | $6.3 \times 10^2$ |
| *S. toyocaensis* 80934/ pOJ402 | ds | $2.9 \times 10^1$ |
| | ss | $1.4 \times 10^3$ |

The results with *S. toyocaensis* 80934 indicate that single-stranded phasmid pOJ401 or pOJ402 DNA transforms at efficiencies 1–2 logs greater than double-stranded DNA. This suggests that single-stranded phasmid pOJ401 and pOJ402 DNA may effectively bypass some restriction systems in a highly restricting strain, such as *S. toyocaensis* 80934.

EXAMPLE 12

Preparation of Plasmid DNA from Streptomyces or *E. coli* Miniprep Procedure

Plasmid DNA is prepared according to a modification of the procedure of Kieser, 1984, Plasmid 12:19–36, as follows. Approximately 1.5 ml of an overnight culture of Streptomyces or *E. coli* is centrifuged and the cells are resuspended in 500 μl of lysozyme solution (for Streptomyces, the solution contains 2 mg/ml lysozyme (Sigma); 0.3M sucrose; 25 mM Tris-HCl, pH 8.0; and 25 mM EDTA, pH 8.0; for *E. coli*, the solution contains all of the above, except lysozyme), and incubated with gentle mixing at 37° C. for Streptomyces or at 0° C. (or no incubation) for *E. coli*. After incubation, 250 μl of an alkaline/SDS solution (0.3M NaOH; 2% SDS) is added, and the suspension is agitated on a vortex mixer to ensure immediate complete mixing. The suspension is then incubated at 70° C. for 10 minutes and cooled to room temperature. Then, 80 μl of phenol:chloroform is added with agitation on a vortex mixer until the phases are thoroughly mixed (~10 seconds), followed by centrifugation for 2 minutes in an Eppendorf centrifuge. The supernatant is removed and placed in a new Eppendorf tube containing 70 μl of 3M unbuffered sodium acetate. To this is added 700 μl of isopropanol with mixing, and the solution is incubated at room temperature for 5 minutes. After incubation, the solution is centrifuged for 5 minutes, the supernatant is decanted, followed by a second centrifugation for 2 seconds to remove all liquid. The DNA pellet is dissolved in 500 μl of TE buffer and 25 μl of 100 mM spermine-HCl is added. After mixing, the DNA solution is incubated at room temperature for 5 minutes, followed by centrifugation as above, with complete removal of the supernatant. The DNA pellet is redissolved in 300 μl of 0.3M sodium acetate and 10 mM MgCl$_2$. Then, 700 μl of cold ethanol is added with mixing followed by room temperature incubation for 5 minutes. The DNA solution is again centrifuged and the supernatant removed completely as above. The DNA pellet is redissolved in 20 μl of TE buffer. The DNA thus obtained may be used for restriction enzyme analysis or for transformation.

EXAMPLE 13

Construction of Phasmid pOJ402

A. Construction of Intermediate Plasmid pOJ107

1. BamHI/PstI Digestion of Plasmid pUC19 DNA

Approximately 1 μg (3 μl) of plasmid pUC19 DNA isolated in substantial accordance with the procedure of Example 2 was added to 1 μl of 10× BamHI buffer (500 mM NaCl; 500 mM Tris-HCl, pH 8.0; 100 mM MgCl$_2$; and 10 mM DTT), 1 μl (about 20 units) of restriction enzyme PstI and 4 μl of H$_2$O and, after gentle mixing, reacted at 37° C. for 1 hour. After reaction, the BamHI/PstI-digested pUC19 DNA was precipitated with ethanol and resuspended in TE buffer.

2. BamHI/PstI Digestion of Cosmid pKC462a DNA

Figure 3:
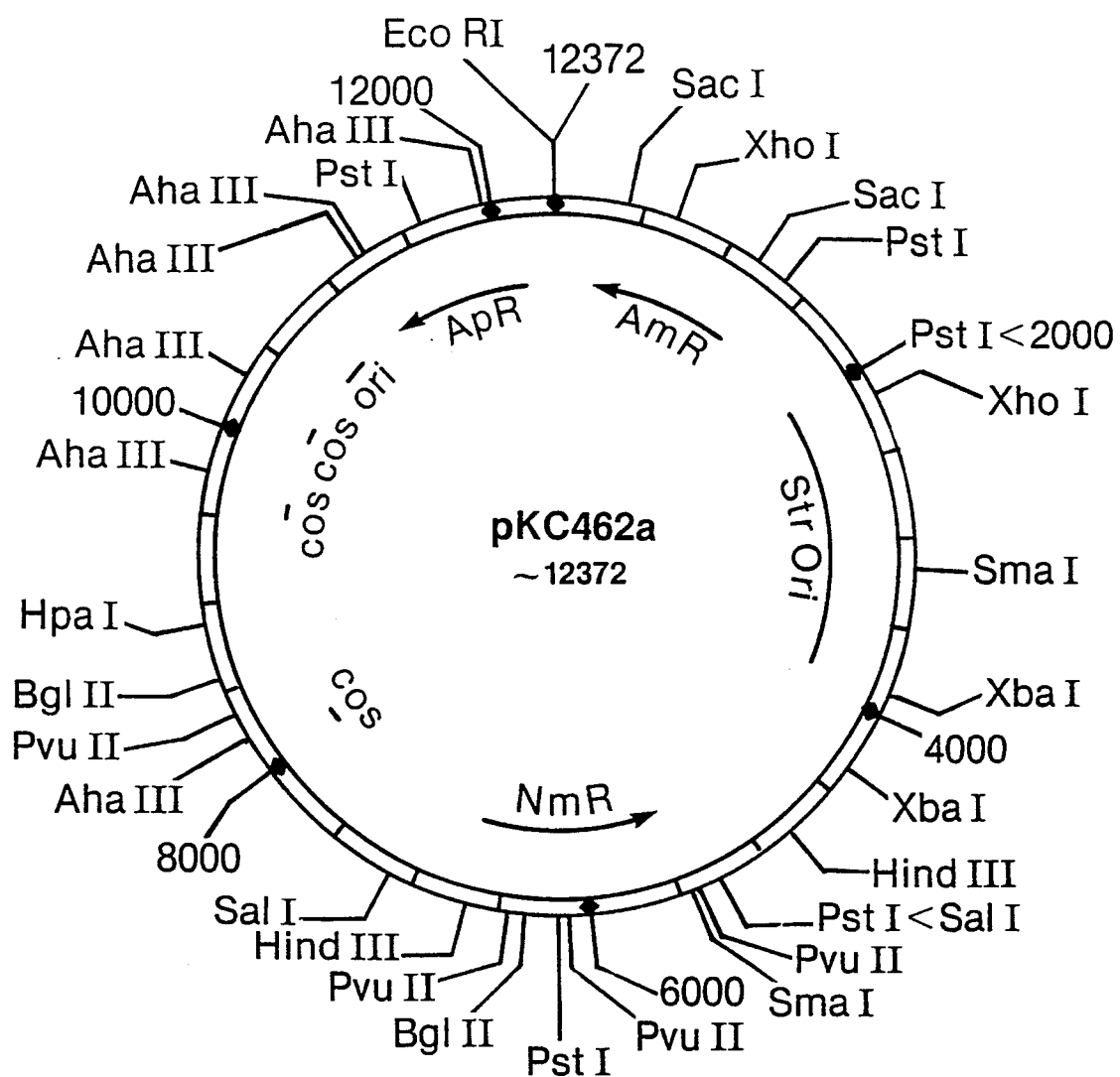

The culture of *E. coli* K12 SF8/pKC462a (NRRL B-15973) and subsequent isolation of cosmid pKC462a DNA were carried out in substantial accordance with the teaching of Example 1. A restriction site and function map of cosmid pKC462a is presented in FIG. 3 of the accompanying drawings. Approximately 10 μg (25 μl) of cosmid pKC462a DNA obtained by this procedure was added to 50 μl of 10× PstI buffer (500 mM NaCl; 500 mM Tris-HCl, pH 8.0; 100 mM MgCl$_2$; and 10 mM DTT), 5 μl (about 100 units) of restriction enzyme PstI and 420 μl of H$_2$O, and reacted after gentle mixing for 3 hours at 37° C. After reacting, the digest was ethanol precipitated and is resuspended in 100 μl of TE buffer and 20 μl of gel-loading buffer (0.25% bromophenol blue; 0.25% xylene cyanol; 15% Ficoll (type 400) in H$_2$O). The PstI-digested DNA was then electrophoresed on a 1% agarose gel. The desired ~2.0 kb PstI fragment of cosmid pKC462a was isolated in substantial accordance with the procedure of Example 3B. The purified fragment was suspended in 50 μl of TE buffer. Then, 10 μl of 10× BamHI buffer was added with 5 μl (about 100 units) of restriction enzyme BamHI and 35 μl of H$_2$O. Incubation was at 37° C. for 2 hours, followed by ethanol precipitation. The BamHI-digested DNA fragment was resuspended in 20 μl of TE buffer, yielding a ~1.7 kb BamHI/PstI fragment from cosmid pKC462a.

3. Ligation of BamHI/PstI-digested Plasmid pUC19 with ~1.7 kb BamHI/PstI fragment of Cosmid pKC462a Approximately 0.1 μg (2 μl) of the BamHI/PstI-digested plasmid pUC19 prepared as described above were added to approximately 1 μg (10 μl) of the ~1.7 kb BamHI/PstI fragment of cosmid pKC462a isolated as described above, and then 2 μl of 10× T4 DNA ligase buffer, 1 μl (about 500 units) of T4 DNA ligase and 5 μl of H$_2$O were added to the DNA. After gentle mixing, the ligation mixture was incubated overnight (~16 hours) at 16° C. This ligation produced intermediate plasmid pOJ107. Approximately 5 μl of the ligation reaction were used to transform *E. coli* K12 JM109 in substantial accordance with the procedure of Example 4 and plasmid DNA was prepared in substantial accordance with the procedure of Example 1B.

B. Construction of Intermediate Plasmid pOJ326

1. BamHI/PstI Digestion of pOJ107

Approximately 5 μg (5 μl) of plasmid pOJ107 isolated as described in part A of this Example were added to 2 μl 10× BamHI buffer, 1 μl (about 20 units) of restriction enzyme BamHI, 1 μl (about 20 units) of restriction enzyme PstI and 11 μl H$_2$O, and reacted at 37° C. for 1 hour. The DNA was precipitated with ethanol and resuspended in 20 μl of TE buffer.

2. PstI/BclI (partial) Digest of pIJ702

Figure 4:
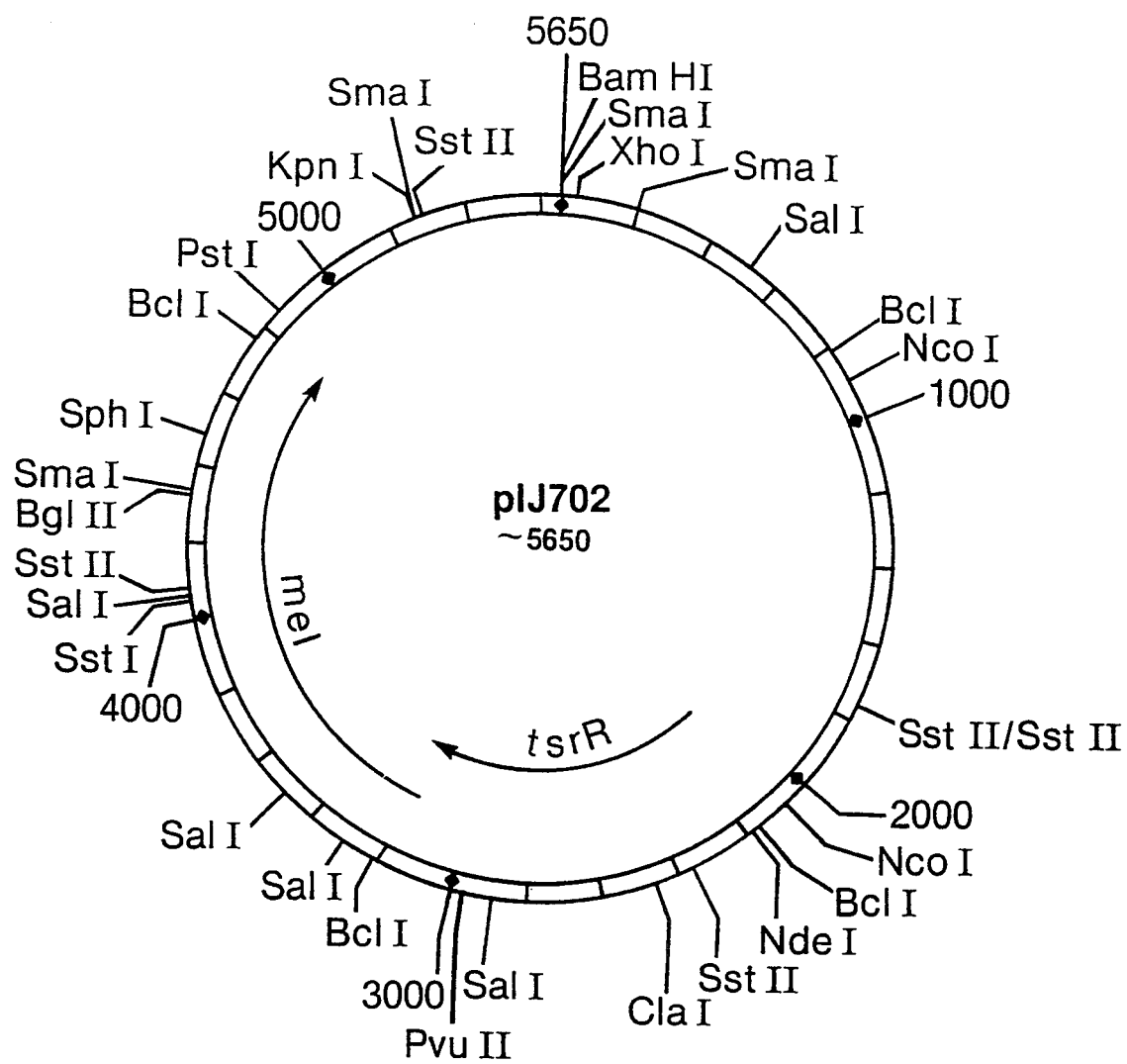
FIG. 4 is a restriction site and function map of plasmid pIJ702.

*Streptomyces lividans*/pIJ702 (ATCC 39155) was cultured and plasmid pIJ702 DNA isolated in substantial accordance with the teaching of Example 1B. Thiostrepton (25 μg/ml) was used to ensure selection of plasmid pIJ702 in the *Streptomyces lividans*/pIJ702 cells. A restriction site and function map of plasmid pIJ702 is presented in FIG. 4 of the accompanying drawings. Approximately 5 μg (5 μl) of plasmid pIJ702 DNA thus obtained were added to 10 μl of 10× restriction enzyme PstI buffer, 1 μl (about 20 units) of PstI, and 84 μl H$_2$O and reacted for 1 hour at 37° C. After reacting, 1 μl (about 10 units) of restriction enzyme BclI was added for 2 minutes at 50° C. The partial digestion was stopped by extracting with equal volumes of phenol and Sevag (24:1 mixture of chloroform:isoamyl alcohol), followed by ethanol precipitation. The DNA was resuspended in 20 μl of TE buffer.

3. Ligation of BamHI/PstI-digested pOJ107 with PstI/BclI (partial) digest of pIJ702

Figure 5:
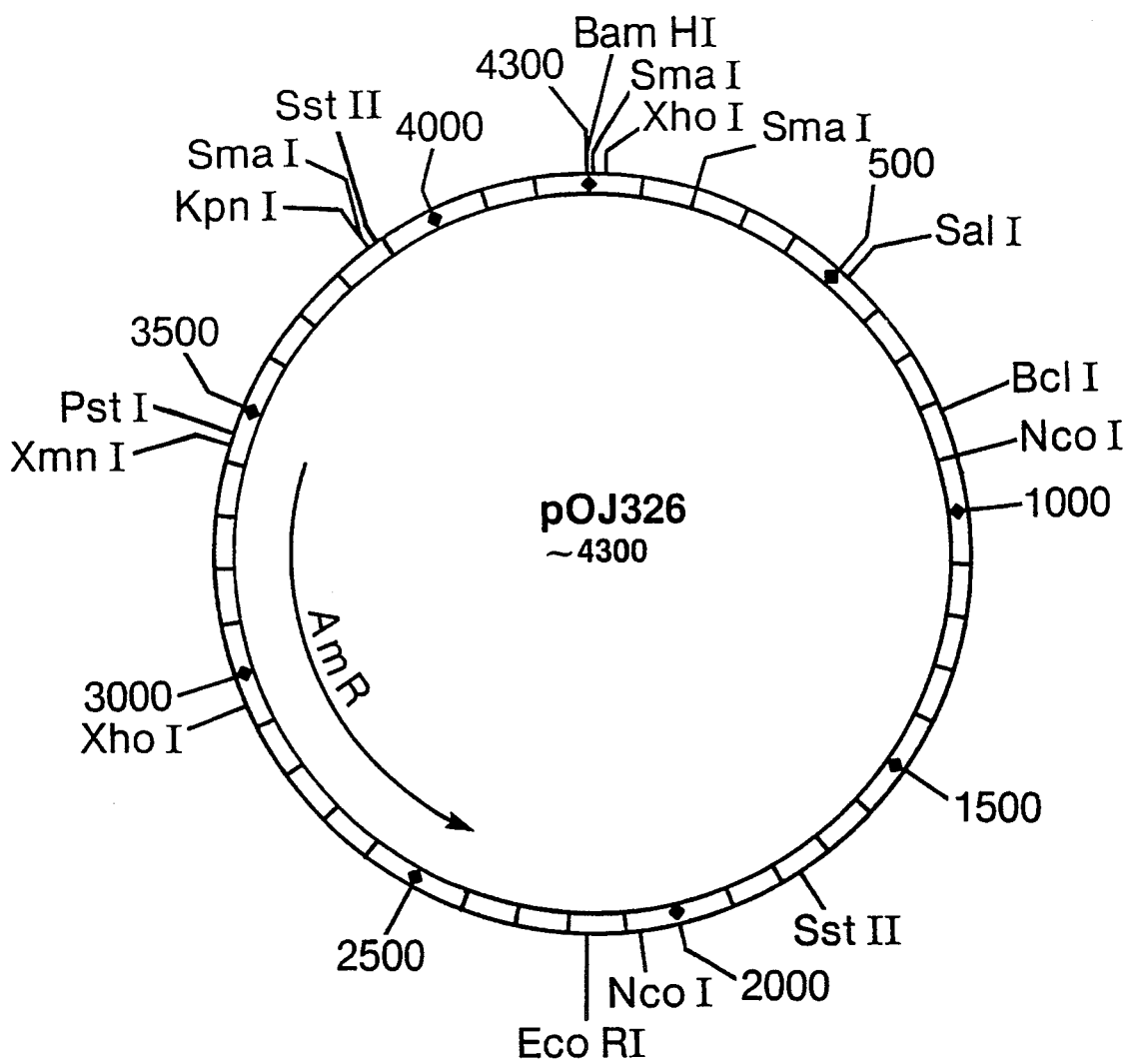
FIG. 5 is a restriction site and function map of plasmid pOJ326.

Approximately 1 μg (4 μl) of the BamHI/PstI-digested plasmid pOJ107 was added to approximately 1 μg (4 μl) of the PstI/BclI(partial) digest of plasmid pIJ702, and then 4 μl of 10× T4 DNA ligase buffer, 1 μl (about 500 units) of T4 DNA ligase and 27 μl H$_2$O were added to the DNA. Incubation was at 16° C. overnight. This ligation produced intermediate plasmid pOJ326. A restriction site and function map of plasmid pOJ326 is presented in FIG. 5 of the accompanying drawings. Approximately 10 μl of the ligation reaction was used to transform *Streptomyces griseofuscus* in substantial accordance with the transformation procedure of Example 8. The R2-agar plates were overlaid with apramycin or thiostrepton to yield a final concentration of 25 μg/ml. The transformants were selected by growth on the apramycin plates but no growth on thiostrepton plates. Transformant colonies were picked, cultured in TSB culture with 25 μg/ml apramycin and plasmid DNA prepared from a 25 ml TSB culture with 25 μg/ml apramycin by the miniprep procedure of Example 12. The miniprep DNA was resuspended in 100 μl of TE buffer and further purified by passing the DNA through a DEAE-cellulose column (Elutip D, Schleicher & Schuell, Inc., 543 Washington Street, Keene, N.H. 03431), ethanol precipitated, and resuspended in 100 μl of TE buffer.

C. Construction of Intermediate Plasmid pOJ328

Approximately 5 μg (40 μl) of plasmid pOJ326 DNA from part B above, were added to 10 μl of 10× EcoRI buffer (500 mM NaCl; 1M Tris-HCl, pH 7.5; 100 mM MgCl$_2$; and 10 mM DTT), 1 μl (about 32 units) of restriction enzyme EcoRI and 51 μl of H$_2$O, and reacted at 37° C. for 1 hour. Then, 1 μl (about 5 units) of Klenow enzyme and 1 μl of a solution containing the 4 dNTPs (each 10 mM) were added and incubation continued for 30 minutes at 37° C. The EcoRI-digested and Klenow-treated DNA was extracted with phenol: Sevag, then ethanol precipitated and resuspended in 50 μl TE.

Approximately 40 μl of the EcoRI-digested, Klenow-treated DNA thus obtained was religated with 5 μl of 10× T4 DNA ligase buffer, 1 μl (about 500 units) T4 DNA ligase and 4 μl H$_2$O at 16° C. overnight. This ligation produced intermediate plasmid pOJ328 and created a second XmnI site in the plasmid. Approximately 40 μl of the ligated DNA solution was again reacted with EcoRI as described above, followed by ethanol precipitation and resuspension in 20 μl of TE buffer. Approximately 10 μl of plasmid pOJ328 DNA were used to transform *Streptomyces griseofuscus* in substantial accordance with the procedure of Example 8 and transformants were selected on TSB plates with 25 μg/ml apramycin. Plasmid pOJ328 DNA was prepared for analysis and use by the miniprep procedure of Example 12.

D. Construction of Intermediate Plasmid pOJ347

1. PvuII/XmnI Digestion of Plasmid pOJ160 DNA and Isolation of ~925 bp Fragment

Approximately 10 μg (10 μl) of plasmid pOJ160 DNA isolated from *E. coli* K12 JM109/pOJ160 (NRRL B-18088) in substantial accordance with the procedure of Example 1, were added to 10 μl of 10× PvuII buffer (500 mM NaCl; 60 mM Tris-HCl, pH 7.5; 60 mM MgCl$_2$; and 10 mM DTT), 1 μl (about 10 units) of restriction enzyme PvuII, 1 μl (about 10 units) of restriction enzyme XmnI and 78 μl of H$_2$O, and reacted at 37° C. for 1 hour. After reacting, the digest was electrophoresed on a 1% agarose gel and the ~900 and ~925 bp fragments were isolated on DEAE paper in substantial accordance with the procedure of Example 3B. The fragments were eluted, ethanol precipitated and resuspended in 20 μl of TE buffer.

2. XmnI Digestion of Plasmid pOJ328

Approximately 1 μg (1 μl) of plasmid pOJ328 DNA obtained in part C above was added to 1 μl of 10× XmnI buffer (same as 10× PvuII buffer), 1 μl (about 10 units) of restriction enzyme XmnI and 7 μl of H₂O, and reacted at 37° C. for 1 hour. After reacting, the DNA was ethanol precipitated and resuspended in 10 μl of TE buffer.

3. Ligation of PvuII/XmnI-Digested Fragments from Plasmid pOJ160 and XmnI-Digested Plasmid pOJ328

Approximately 1 μg (10 μl) of XmnI-digested plasmid pOJ328 DNA prepared as above was added to approximately 1 μg (5 μl) of the ~900 and ~925 kb PvuII-XmnI fragments of pOJ160 isolated as above, and then 4 μl of 10× T4 DNA ligase buffer, 1 μl (about 500 units) of T4 DNA ligase and 20 μl of H₂O were added to the DNA. After gentle mixing, the ligation mixture was incubated overnight (~16 hours) at 16° C. This ligation produced intermediate plasmid pOJ347. Approximately 10 μl of the ligation reaction was used to transform *E. coli* K12 JM109 in substantial accordance with the procedure of Example 4. The transformants were selected by plating on TAXI-plates at 37° C. overnight. Plasmid pOJ347 DNA was prepared in substantial accordance with the procedure of Example 1B.

E. Construction of Intermediate Plasmid pOJ348

Approximately 5 μg (5 μl) of plasmid pOJ347 DNA obtained in part D above were added to 2 μl of 10× NdeI buffer (1.5M NaCl; 16 mM Tris-HCl, pH 7.5; 60 mM MgCl₂; and 10 mM DTT), 1 μl (about 5 units) of restriction enzyme NdeI, 1 μl (about 5 units) of restriction enzyme NruI (according to the NEB catalog, NruI contains a contaminating exonuclease; this permits exonuclease removal of the NdeI sticky ends), and 11 μl of H₂O, and reacted at 37° C. for 2 hours. After reacting, the digest was precipitated with ethanol and resuspended in 20 μl of TE.

Figure 6:
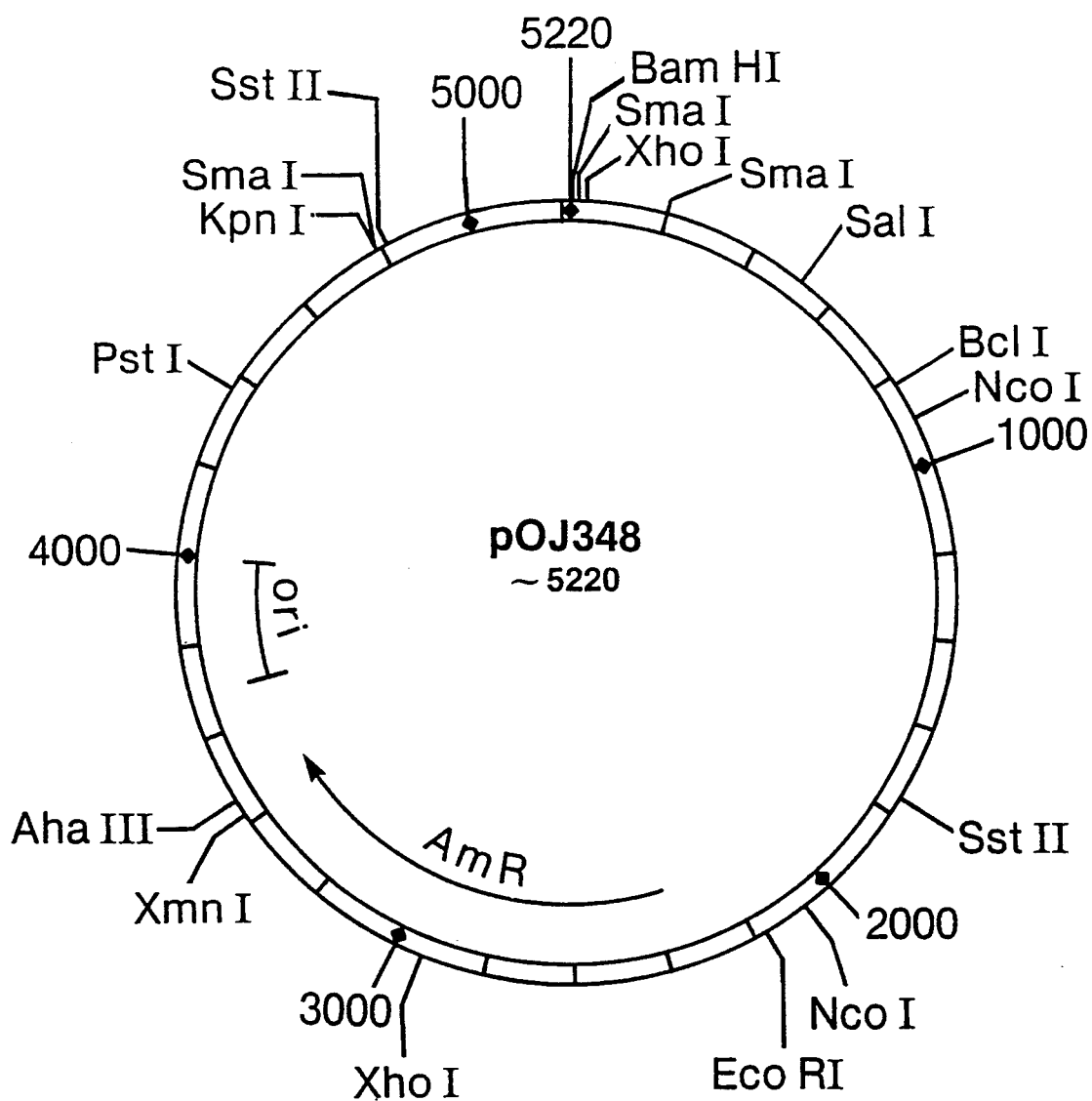
FIG. 6 is a restriction site and function map of plasmid pOJ348.

The 20 μl of NdeI/NruI-digested plasmid pOJ347 DNA was then added to 4 μl of 10× T4 DNA ligase buffer, 1 μl (about 500 units) of T4 DNA ligase, 4 μl of 10 mM ATP and 11 μl of H₂O. The ligation reaction was incubated at 16° C. overnight and produced intermediate plasmid pOJ348. A restriction site and function map of plasmid pOJ348 is presented in FIG. 6 of the accompanying drawings. This step was necessary to remove ~700 bp of the unwanted ~900 bp PvuII fragment containing a thiostrepton resistance gene that was ligated along with the desired ~925 bp fragment from plasmid pOJ160 in the prior step described in part D above.

Approximately 10 μl of the ligation reaction was used to transform *E. coli* K12 JM109 in substantial accordance with the procedure of Example 4; transformants were selected on TY-agar plates with 200 μg/ml apramycin, grown overnight at 37° C. Plasmid DNA for analysis and use was prepared in substantial accordance with the procedure of Example 1B or Example 12.

F. Construction of Intermediate Plasmid pOJ352

1. KpnI Digestion of Plasmid pOJ348 DNA

Approximately 5 μg (5 μl) of plasmid pOJ348 DNA, prepared as in part E above, were added to 10 μl of 10× KpnI buffer (60 mM NaCl; 60 mM Tris-HCl, pH 7.5; 60 mM MgCl₂; and 10 mM DTT), 1 μl (about 15 units) of restriction enzyme KpnI, and 84 μl of H₂O, and reacted at 37° C. for 1 hour. After reacting, the DNA was precipitated with ethanol and resuspended in 20 μl of TE buffer.

2. Treatment with Mung Bean Nuclease

Approximately 1 μg (5 μl) of the KpnI-digested plasmid pOJ348 DNA was added to 10 μl of 10× Mung Bean Nuclease buffer (300 mM sodium acetate, pH 4.6; 500 mM NaCl; and 10 mM ZnCl₂), 1 μl (about 100 units) of Mung Bean Nuclease (freshly diluted 1:10 in 1× buffer), 84 μl of H₂O, and reacted at 37° C. for 10 minutes. After reacting, the DNA was twice extracted with TE saturated phenol, ethanol precipitated, and resuspended in 20 μl of TE buffer.

3. Ligation of KpnI-Digested, Mung Bean Nuclease-Treated Plasmid pOJ348 DNA

Figure 7:
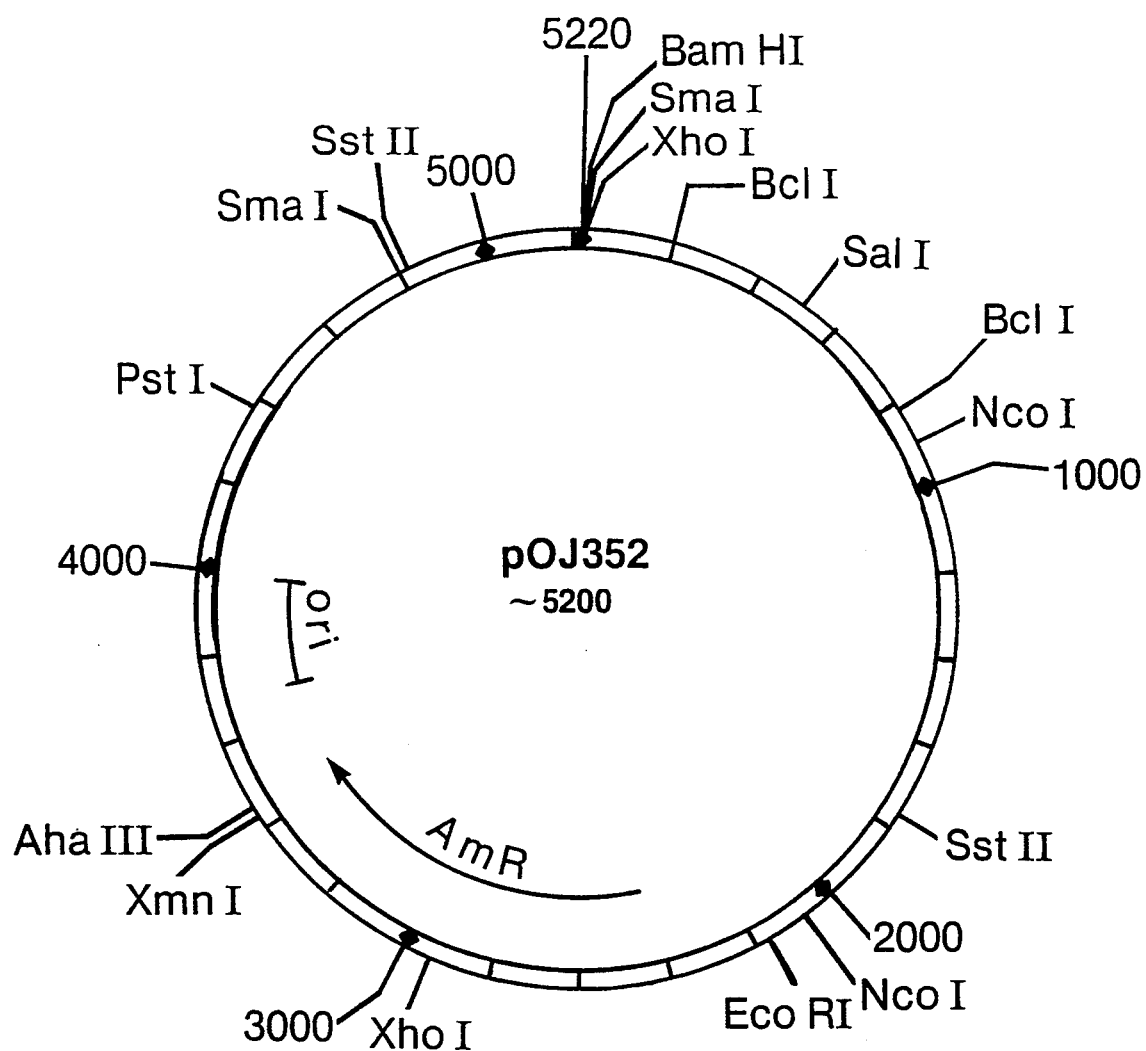
FIG. 7 is a restriction site and function map of plasmid pOJ352.

Approximately 0.3 μg (10 μl) of the KpnI-digested, Mung Bean Nuclease-treated plasmid pOJ348 DNA was added to 10 μl of 10× T4 DNA ligase buffer, 1 μl (about 500 units) of T4 DNA ligase, 79 μl of H₂O, and incubated at 37° C. overnight for blunt-end ligation. This ligation produced intermediate plasmid pOJ352. A restriction site and function map of plasmid pOJ352 is presented in FIG. 7 of the accompanying drawings. Approximately 20 μl of the ligation reaction were used to transform *E. coli* K12 JM109 in substantial accordance with the procedure of Example 4. Transformants were selected on TY-agar plates containing 200 μg/ml apramycin. Plasmid pOJ352 DNA was prepared for restriction enzyme analysis and subsequent use in substantial accordance with the procedure of Example 1B or Example 12.

G. Construction of Intermediate Plasmid pOJ354

1. EcoRI Digestion of Plasmid pOJ352 DNA

Approximately 5 μg (5 μl) of plasmid pOJ352 DNA, prepared as in part F above, were added to 10 μl of 10× EcoRI buffer, 1 μl (about 20 units) of restriction enzyme EcoRI, 84 μl of H₂O, and reacted at 37° C. for 2 hours. After reacting, the DNA was precipitated with ethanol and resuspended in 20 μl of TE buffer.

2. Treatment with Mung Bean Nuclease

Approximately 1 μg (5 μl) of he EcoRI-digested plasmid pOJ352 DNA was treated with Mung Bean Nuclease in substantial accordance with the procedure of part F above, except that the incubation was for 2 hours, rather than 10 minutes. The Mung Bean Nuclease-treated DNA was resuspended in 20 μl of TE buffer.

3. Ligation of EcoRI-digested, Mung Bean Nuclease-Treated Plasmid pOJ352 DNA

Approximately 0.1 μg (10 μl) of the EcoRI-digested, Mung Bean Nuclease-treated plasmid pOJ352 DNA was ligated in substantial accordance with the procedure of part F above. The ligation produced the intermediate plasmid pOJ354. Approximately 10 μl of the 40 μl ligation reaction was used to transform *E. coli* K12 JM109 in substantial accordance with the procedure of Example 4. Transformants were selected on TY-agar plates containing 200 μg/ml apramycin. Plasmid pOJ354 DNA was prepared for restriction enzyme analysis and subsequence use in substantial accordance with procedure of Example 1B or Example 12.

H. Construction of Intermediate Plasmid pOJ355

1. PstI Digestion of Plasmid pOJ354 DNA

Approximately 5 μg (5 μl) of plasmid pOJ354 DNA, prepared as in part G above, were added to 10 μl of 10× PstI buffer, 1 μl (about 30 units) of restriction enzyme PstI, and 84 μl of H₂O, and reacted at 37° C. for 2 hours. After reacting, the DNA was precipitated with ethanol and resuspended in 20 μl of TE buffer.

2. Preparation of Annealed Polylinker

The single-stranded DNA fragments used in the construction of a polylinker were chemically synthesized either by using a Systec 1450A DNA Synthesizer (Systec, Inc., 3816 Chandler Drive, Minneapolis, Minn. 55401) or an ABS 380A DNA Synthesizer (Applied Biosystems, Inc., 850 Lincoln Centre Drive, Foster City, Calif. 94404). Many DNA synthesizing instruments are known in the art and can be used to make the fragments. In addition, the fragments can also be conventionally prepared in substantial accordance with the procedures of Itakura et al., 1977, Science, 198:1056 and Crea et al., 1978, Proc. Nat. Acad. Sci. U.S.A., 75: 5765.

Strand 1 (designated #806, 28.58 pM/μl) and strand 2 (designated #807, 18.39 pM/μl) were annealed after synthesis of the single strands as follows. Eighteen μl (~500 pM) of strand 1 and 28 μl of strand 2 (~500 pM) were mixed together in an Eppendorf tube, and 3 μl of 10× TM buffer (0.5M Tris-HCl pH=7.6, 0.1M MgCl$_2$) were added. The tube was placed in a boiling water bath, removed from the boiling water and allowed to cool slowly at room temperature, then placed overnight at 4° C. This process annealed the single strands to form the double-stranded polylinker. The polylinker so constructed had the following structure:

```
5'-GAAGCTTGCATGCTCTAGAAGATCTAGTACTGGTACCGAATTCATGCA-3'
   |||||||||||||||||||||||||||||||||||||||||||||||
3'-ACGTCTTCGAACGTACGAGATCTTCTAGATCATGACCATGGCTTAAGT-5'
``` and contains the following restriction enzyme sites: PstI, HindIII, SphI, XbaI, BglII, ScaI, KpnI, EcoRI, and NsiI.

3. Ligation of PstI-Digested Plasmid pOJ354 DNA and Polylinker

Figure 8:
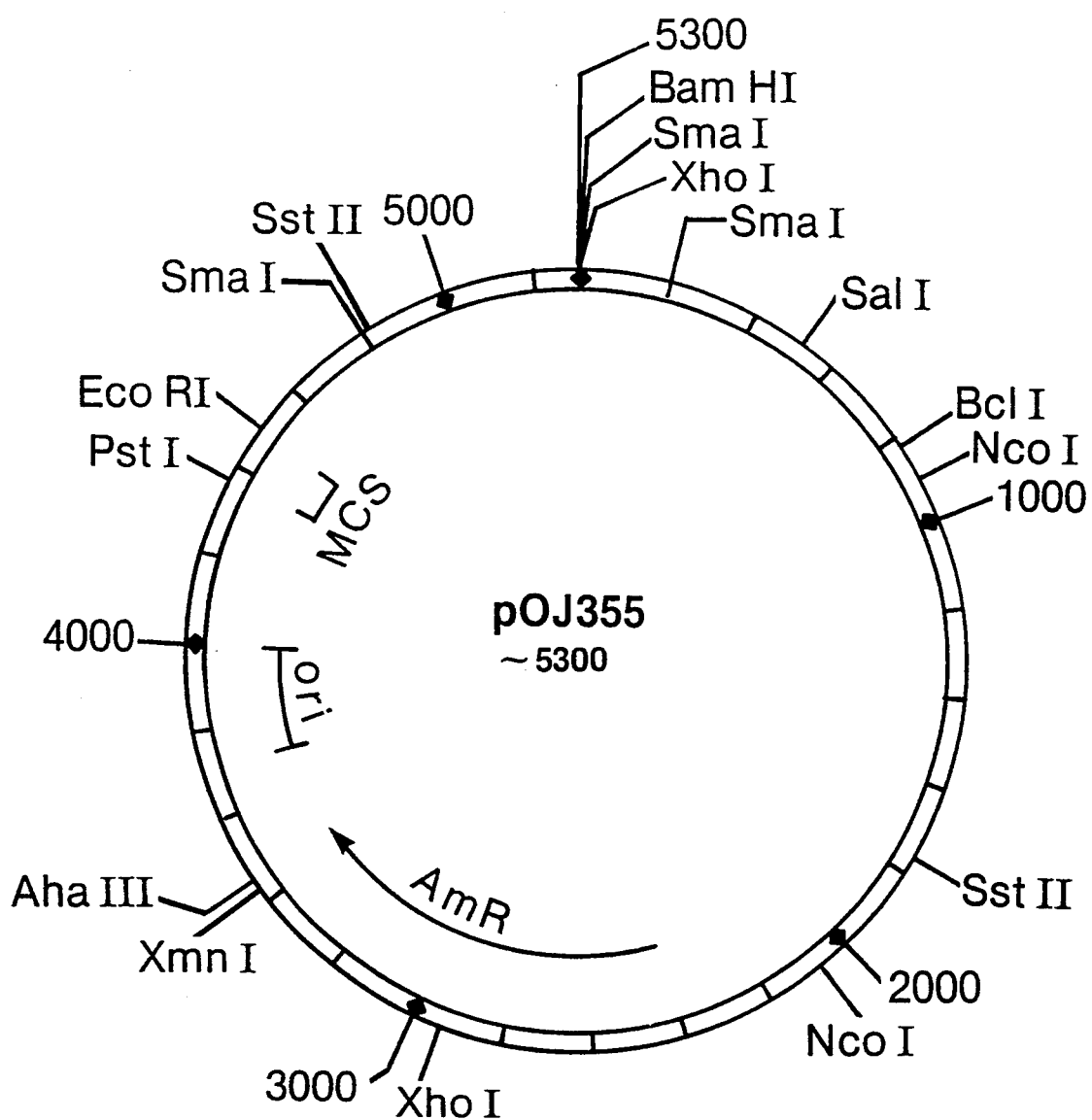
FIG. 8 is a restriction site and function map of plasmid pOJ355.

Approximately 1 μg (5 μl) of PstI-digested plasmid pOJ354 DNA was added to 4 μl of annealed polylinker prepared above, 4 μl of 10× T4 DNA ligase, and 26 μl of H$_2$O, and incubated overnight at 16° C. The ligation produced plasmids pOJ355 and pOJ356, which differ only with respect to the orientation of the polylinker. A restriction site and function map of plasmid pOJ355 is presented in FIG. 8 of the accompanying drawings. Approximately 10 μl of the ligation reaction were used to transform E. coli K12 JM109 in substantial accordance with the procedure of Example 4. Transformants were selected on TY-agar plates with 200 μg/ml apramycin. Plasmids pOJ355 and pOJ356 DNA were prepared for restriction analysis and subsequent use in substantial accordance with the procedure of Example 1B or Example 12.

I. Construction of Intermediate Plasmid pOJ361

1. DraI-Digestion of Plasmid pOJ355

Approximately 5 μg (5 μl) of plasmid pOJ355 DNA, prepared as in part H above, were added to 10 μl of 10× DraI buffer (60 mM NaCl; 60 mM Tris-HCl, pH 7.5; 60 mM MgCl$_2$; and 10 mM DTT), 1 μl (about 20 units) of restriction enzyme DraI (an isoschizomer of AhaIII), and 84 μl of H$_2$O, and reacted at 37° C. for 1 hour. After reacting, the DNA was precipitated with ethanol and resuspended in 20 μl of TE buffer.

2. BclI-Digestion and Klenow-Treatment of Plasmid pIJ702 DNA, and Isolation of ~1 kb Fragment Approximately 5 μg (5 μl) of plasmid pIJ702 DNA (part B of this Example) were added to 10 μl of 10× BclI buffer (500 mM NaCl; 500 mM Tris-HCl, pH 8.0; 100 mM MgCl$_2$; and 10 mM DTT), 1 μl (about 10 units) of restriction enzyme BclI, and 84 μl of H$_2$O, and reacted at 50° C. for 1 hour. The digestion was stopped by heat inactivation at 70° C. for 1 hour.

The BclI-digested plasmid pIJ702 DNA was treated with Klenow enzyme in substantial accordance with the procedure of Example 3B. The BclI-digested, Klenow-treated plasmid pIJ702 DNA was then electrophoresed on a 1% agarose gel. An ~1 kb BclI (Klenow) fragment was isolated in substantial accordance with the procedure of Example 3B. The fragment was resuspended in 20 μl of TE buffer.

Figure 9:
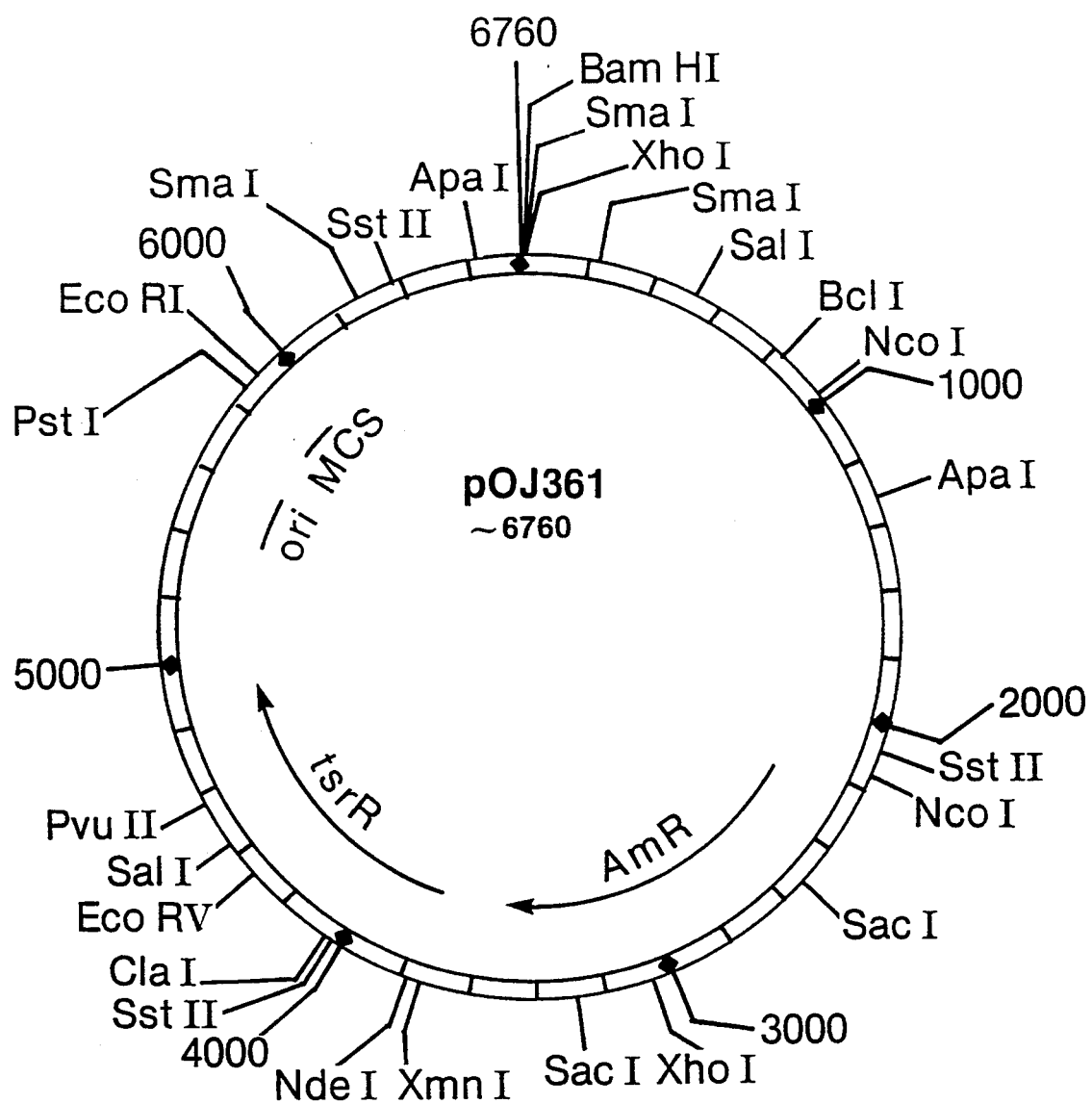
FIG. 9 is a restriction site and function map of plasmid pOJ361.

3. Ligation of DraI-Digested Plasmid pOJ355 and BclI (Klenow)-digested Plasmid pIJ702 DNA Approximately 1 μg (5 μl) of DraI-digested plasmid pOJ355 was added to 2 μl (about 0.1 μg) of BclI (Klenow)-digested plasmid pIJ702, 4 μl of 10× T4 DNA ligase buffer, 1 μl (about 500 units) of T4 DNA ligase, and 32 μl of H$_2$O, and incubated at 37° C. overnight for blunt ligation. The ligation produced intermediate plasmid pOJ361. A restriction site and function map of plasmid pOJ361 is presented in FIG. 9 of the accompanying drawings.

Approximately 10 μl of the ligation reaction were used to transform S. griseofuscus in substantial accordance with the procedure of Example 8. Transformants were selected on R2 agar plates with 25 μg/ml thiostrepton. A colony was picked from the plates and grown overnight in TSB with 25 μg/ml thiostrepton. Plasmid pOJ361 DNA was prepared for restriction analysis and transformation in substantial accordance with the procedure of Example 12. Plasmid pOJ361 DNA thus obtained was resuspended in 20 μl of TE buffer. Approximately 5 μl of the DNA were used to transform E. coli K12 JM109 in substantial accordance with the procedure of Example 4. The transformants were selected on TY-agar plates with 200 μg/ml apramycin. Resulting colonies were picked and plasmid DNA prepared in substantial accordance with the procedure of Example 12.

J. Construction of Phasmid pOJ402

1. AhaIII-Digestion of Plasmid pBluescript SK+

Approximately 3 μg (3 μl) of plasmid pBluescript SK+ DNA (Example 1) were added to 10 μl of 10× AhaIII buffer, 1 μl (about 20 units) of restriction enzyme AhaIII (an isoschizomer of DraI) and 86 μl of H$_2$O, and reacted at 37° C. for 2 hours. After reacting, the DNA was precipitated with ethanol and resuspended in 20 μl of TE buffer.

2. XmnI/EcoRI-Digestion of Plasmid pOJ361 DNA, Klenow Treatment and Isolation of ~4.5 kb Fragment Approximately 10 μg (10 μl) of plasmid pOJ361 DNA (part I above) were added to 10 μl of 10× XmnI buffer, 1 μl (about 10 units) of restriction enzyme XmnI, 79 μl of H$_2$O, and reacted at 37° C. for 1 hour. Then, 11 μl of 10× EcoRI buffer and 1 μl (about 20 units) of restriction enzyme EcoRI were added to the XmnI digestion, and incubation continued at 37° C. for 2 hours.

The XmnI/EcoRI-digested plasmid pOJ361 DNA was treated with Klenow-enzyme in substantial accordance with the procedure of Example 3B, and the Klenow-treated digest was then electrophoresed on a 1% agarose gel. An ~4.5 kb XmnI/EcoRI (Klenow) fragment was isolated in substantial accordance with the procedure of Example 3A, and resuspended in 20 μl of TE buffer.

Figure 10:
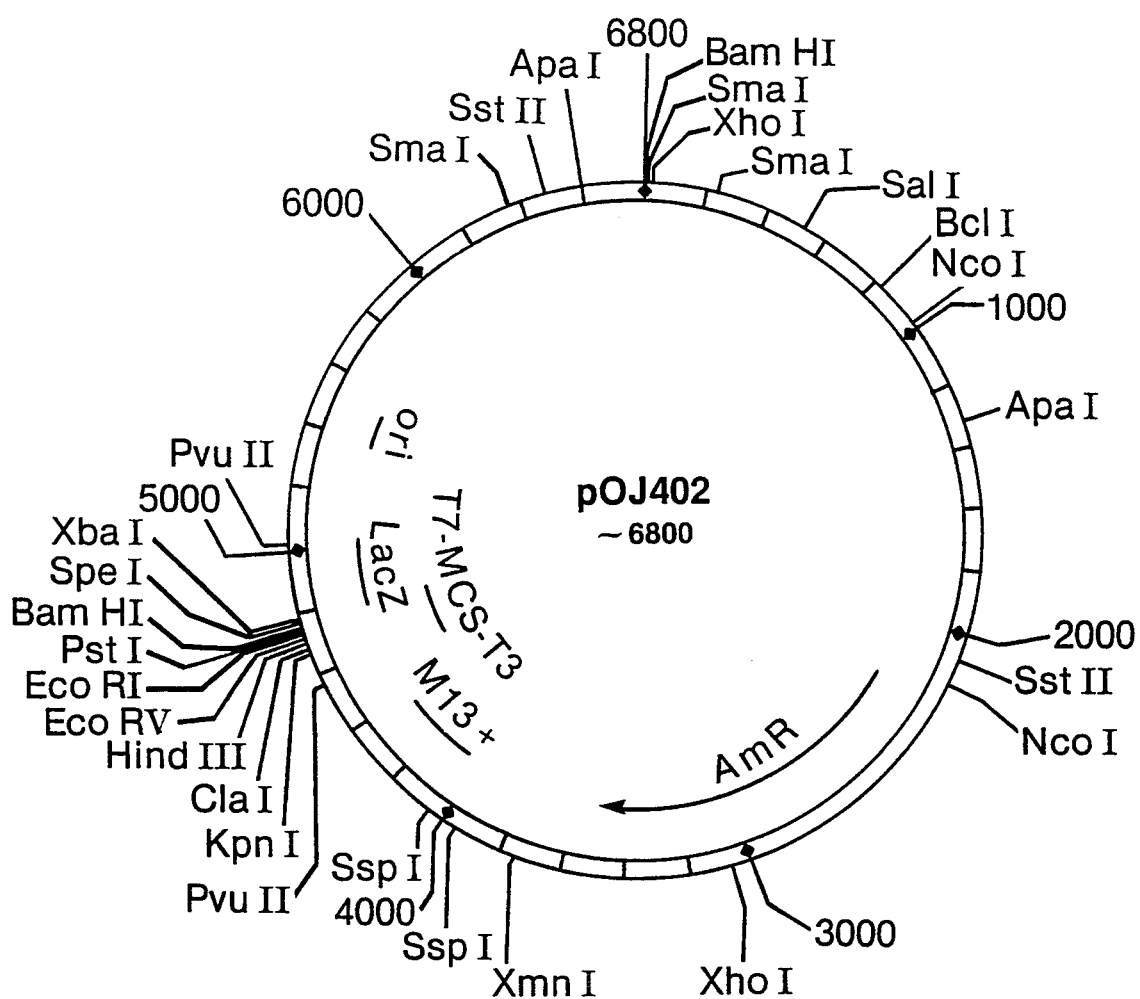
FIG. 10 is a restriction site and function map of phasmid pOJ402.

3. Ligation of ~4.5 kb XmnI/EcoRI (Klenow) Fragment of Plasmid pOJ361 DNA and AhaIII-Digested Plasmid pBluescript SK+ DNA Approximately 0.5 μg (5 μl) of the ~4.5 kb XmnI/EcoRI (Klenow) fragment of plasmid pOJ361 DNA was added to 5 μl (about 0.15 μg) of AhaIII-digested plasmid pBluescript SK+ DNA, 4 μl of 10× T4 DNA ligase buffer, 1 μl (about 500 units) of T4 DNA ligase, 25 μl of H2O, and incubated at 37° C. overnight for blunt ligation. The ligation produced the desired phasmid pOJ402. A restriction site and function map of phasmid pOJ402 is presented in FIG. 10 of the accompanying drawings.

Approximately 10 μl of the ligation reaction were used to transform *E. coli* K12 RR1 in substantial accordance with the procedure of Example 4. Transformants were selected on TAXI-plates. Phasmid pOJ402 DNA was prepared for restriction enzyme analysis and for subsequent transformation into *E. coli* K12 JM109 in substantial accordance with the procedure of Example 12.

EXAMPLE 14

Construction of Plasmid pOJ192

A. Construction of Intermediate Plasmid pOJ189

1. XmnI/HindIII Digestion of Plasmid pOJ160 DNA and Isolation of ~5.9 kb Fragment Approximately 20 μg (20 μl) of plasmid pOJ160 DNA (Example 1) were added to 10 μl of 10× XmnI buffer, 3 μl (about 18 units) of restriction enzyme XmnI, 3 μl (about 60 units) of restriction enzyme HindIII, 64 μl of H2O, and reacted at 37° C. for 2 hours. The digest was electrophoresed on a 1% agarose gel and the ~5.9 kb XmnI/HindIII fragment was isolated in substantial accordance with the procedure of Example 3B. The ~5.9 kb fragment was resuspended in 20 μl of TE buffer.

2. EcoRI/HindIII Digestion and Klenow-Treatment of Cosmid pKC462a DNA

Approximately 30 μg (15 μl) of cosmid pKC462a DNA (Example 13A) were added to 10 μl of 10× EcoRI buffer, 3 μl (about 15 units) of restriction enzyme EcoRI, 72 of H2O, and reacted at 37° C. for 3 hours. The EcoRI-digest was then treated with Klenow enzyme in substantial accordance with the procedure of Example 3B. After Klenow-treatment, the DNA was precipitated wth ethanol, resuspended in 100 μl of 1× HindIII buffer and 3 μl (about 60 units) of restriction enzyme HindIII were added. The reaction was incubated at 37° C. for 2 hours, and then electrophoresed on a 1% agarose gel. An ~5.7 kb EcoRI(Klenow)/HindIII fragment was isolated from the gel in substantial accordance with the procedure of Example 3B, and resuspended in 20 μl of TE buffer.

3. Ligation of ~5 9 kb XmnI/HindIII Fragment of Plasmid pOJ160 and ~5.7 kb EcoRI(Klenow)/HindIII Fragment of Cosmid pKC462a Approximately 2 μg (4 μl) of the ~5.9 kb XmnI/HindIII fragment of plasmid pOJ160 and approximately 2 μg (4 μl) of the ~5.7 kb EcoRI (Klenow)/HindIII fragment of cosmid pKC462a were added to 4 μl of 10× T4 DNA ligase buffer, 1 μl (about 500 units) of T4 DNA ligase and 27 μl of H2O. The ligation reaction was incubated overnight at 16° C. The ligation produced intermediate plasmid pOJ189.

Approximately 10 μl of the ligation reaction were used to transform *E. coli* K12 JM109 in substantial accordance with the procedure of Example 4. Transformants were selected at 30° C. on TAXI-plates. Plasmid pOJ189 DNA was prepared for restriction enzyme analysis and subsequent use in substantial accordance with the procedure of Example 1B or Example 12.

B. Construction of Plasmid pOJ192

Approximately 20 μg (20 μl) of plasmid pOJ189 DNA prepared in part A above, were added to 10 μl of 10× AhaIII buffer, 2 μl (about 6 units) of restriction enzyme AhaIII, 68 μl of H2O, and reacted at 37° C. for 8 minutes. After the partial AhaIII digestion, the DNA was precipitated with ethanol and resuspended in 20 μl of TE buffer.

Approximately 2 μg (2 μl) of the AhaIII (partial) digest of pOJ189 DNA were added to 4 μl of 10× T4 DNA ligase buffer, 1 μl (about 500 units) of T4 DNA ligase, 33 μl of H2O, and incubated at 16° C. overnight. After incubation, the reaction was heat-inactivated at 70° C. for 20 minutes. The 40 μl ligation reaction was then added to 10 μl of 10× ScaI buffer (50 mM NaCl; 60 mM Tris-HCl pH 7.5; 60 mM MgCl2; and 10 mM DTT), 3 μl (about 30 units) of restriction enzyme ScaI, 50 μl of H2O, and reacted at 37° C. for 2 hours. The ScaI-treated ligation mixture contained the desired plasmid pOJ192. After the ScaI treatment, the DNA was precipitated with ethanol and resuspended in 40 μl of TE buffer.

Figure 11:
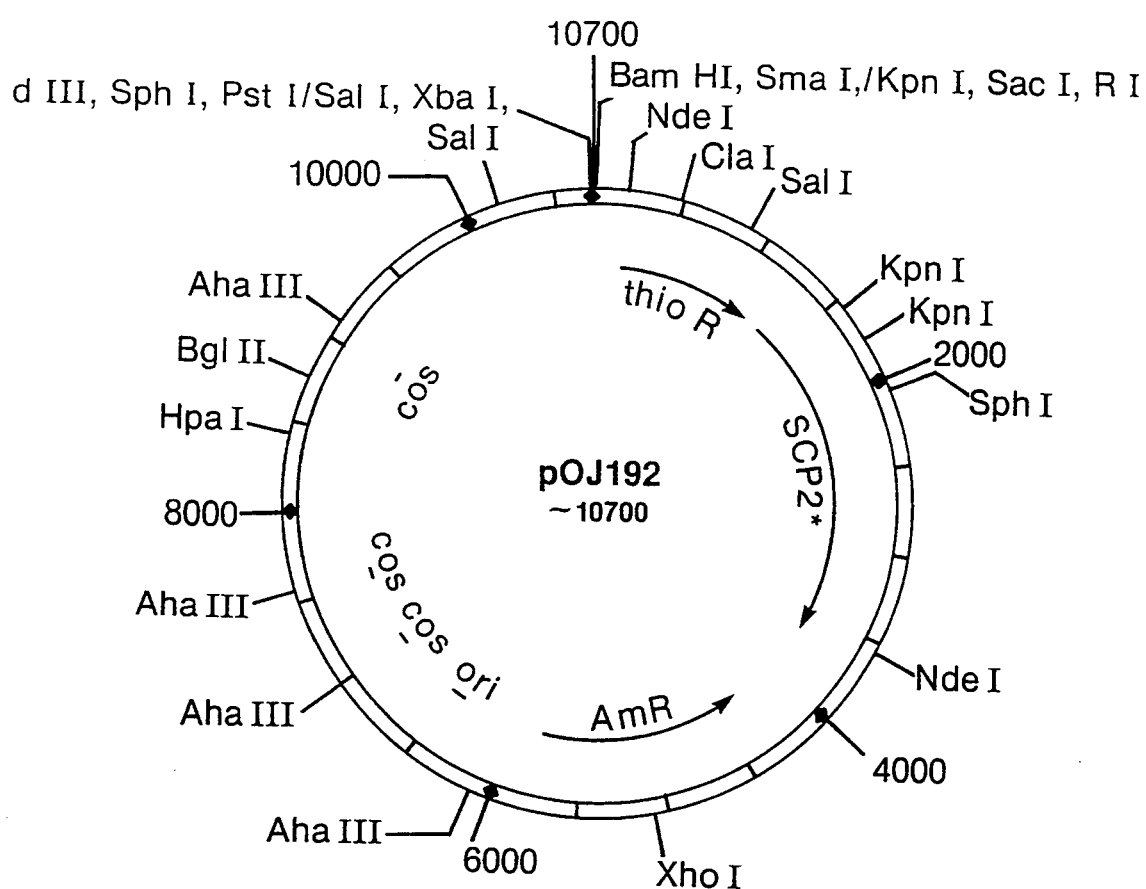
FIG. 11 is a restriction site and function map of plasmid pOJ192.

Approximately 10 μl of ScaI-treated plasmid pOJ189 DNA that was AhaIII-digested and ligated were used to transform *E. coli* K12 JM109 in substantial accordance with the procedure of Example 4. *E. coli* K12 JM109/pOJ192 transformants were selected at 30° C. on TY-agar plates with 200 μg/ml apramycin. The apramycin-resistant *E. coli* K12 JM109/pOJ192 transformants were also plated on TY-agar with 100 μg/ml ampicillin to confirm ampicillin sensitivity, due to the deletion of the ampicillin-resistance gene from plasmid pOJ189 during the construction and selection of desired plasmid pOJ192. A restriction site and function map of plasmid pOJ192 is presented in FIG. 11 of the accompanying drawings.

Plasmid pOJ192 DNA was prepared for use in constructing a *Streptomyces felleus* library, as described below in Example 15, in substantial accordance with the procedure of Example 1B.

EXAMPLE 15

The Construction of a *Streptomyces felleus* Genomic Library

A. Preparation of the Vector pOJ192 DNA

About 30 μg (30 μl) of plasmid pOJ192 DNA were digested in 10 μl of 10× HpaI buffer (100 mM Tris-HCl pH 7.5; 100 mM MgCl2; 10 mM KCl; and 1 mM DTT), with 10 μl (about 50 units) of restriction enzyme HpaI, and 50 μl of H2O for 3 hours at 37° C. About 2.5 units (25 μl) of BAP (bacterial alkaline phosphatase) (International Biotechnologies, Inc., P.O. Box 1565, New Haven, Conn. 06506) were added and incubated for 2 hours at 60° C. The DNA was extracted twice with phenol, twice with Sevag and precipitated with ethanol. The DNA was then resuspended in 100 μl of TE buffer; 50 μl of the resuspended DNA were digested in 10 μl of 10× BamHI buffer with 5 μl (about 50 units) of restriction enzyme BamHI and 35 µl of H₂O for 3 hours at 37° C. The DNA was again extracted with phenol, Sevag, precipitated with ethanol, as above, and finally resuspended in 50 µl of TE buffer.

B. Preparation of the Insert DNA

*Streptomyces felleus* (NRRL 2251) was grown in 250 ml of TSB supplemented with 100 µg of spiramycin (Sigma) for 16 hours at 30° C. The cells were harvested by centrifugation (10 minutes at 8,000 rpm) suspended in 10 ml of lysis mix (300 mM sucrose, 25 mM Tris-HCl pH 8.0, and 25 mM EDTA) and brought to a final concentration of 1 mg/ml with lysozyme and incubated at 37° C. for 10 minutes. Then proteinase K was added to a final concentration of 200 µg/ml and SDS (sodium dodecyl sulfate) was added to a final concentration of 2%. The mixture was incubated at 70° C. for 10 minutes and then cooled on ice. The mixture was made 1M in potassium acetate and left on ice for 30 minutes. After gently extracting the material with TE saturated phenol, the layers were separated and the aqueous layer was gently extracted with Sevag. Layers were again separated and the nucleic acids in the aqueous layer were precipitated with ethanol. The precipitate was washed with 70% ethanol and then dissolved in 5 ml of TE buffer. RNase A was added to the DNA solution to a final concentration of 50 µg/ml. This solution was then incubated at 37° C. for 30 minutes, extracted twice with phenol, twice with Sevag and then precipitated with ethanol. The DNA was redissolved in 1 ml of TE buffer (545 µg/ml) and then sized on a 0.3% agarose gel with λ DNA size standards and was found to have an average size greater than 70 kb.

Next, about 50 µg (100 µl) of *Streptomyces felleus* chromosomal DNA were incubated with 30 units of MboI in 500 µl of 1× MboI buffer (100 mM NaCl; 10 mM Tris-HCl; pH 7.4; 10 mM MgCl₂; and 1 mM DDT) at 37° C. for 15 minutes. This particular condition was found empirically to give the desired partial fragmentation of chromosomal DNA. The DNA was extracted with phenol, Sevag and then dissolved in 100 µl of TE buffer.

About 25 µg of *Streptomyces felleus* MboI partials were subsequently treated with BAP (2.5 units for 3 hours at 70° C.) in 500 µl of 1× BAP buffer. The DNA was extracted with phenol, Sevag, precipitated with ethanol and then dissolved in 100 µl of TE buffer. The size of this DNA was estimated on a 0.3% agarose gel and was found to be 30–40 kb.

C. Ligation of the Vector DNA to the Insert DNA

About 125 ng (4 µl) of pOJ192 DNA (prepared in part A of this Example) were mixed with 500 ng (4 µl) of *Streptomyces felleus* MboI partials (prepared in part B of this Example) and ligated with approximately 400 units of T4 DNA ligase in 4 µl of 10× ligase buffer made 1 mM in ATP. Ligation was performed for 16 hours at 16° C.

D. In Vitro Packaging

Packaging was performed by adding about 4 µl of the ligation mixture (∼62.5 ng of hybrid vector DNA) to a GIGAPACK packaging kit (Stratagene) at room temperature for 2 hours. To this mixture, about 500 µl of phage buffer (10 mM Tris-HCl, pH 7.4; 10 mM MgSO₄; and 0.01% gelatin) were added.

E. Transduction of *E. coli* K12 SF8

About 200 µl of packaged cosmids (25 ng of vector DNA) were adsorbed to 500 µl of *E. coli* K12 SF8 cells grown in tryptone yeast extract supplemented with 0.2% maltose and 10 mM magnesium sulfate. Adsorption was done for 10 minutes at 37° C. in 10 mM Tris, pH 8.0, and 10mM MgSO₄. The cells were grown in 5 ml of TY broth for 2 hours at 30° C. and transductants were selected at 30° C. on TY plates supplemented with 200 µg/ml of apramycin. Approximately 6,000 colonies resulted from the plating of 0.1 ml of transduced cells, giving rise to a transducing efficiency of about 2×10⁶ transductants per microgram.

F. Transformation into *Streptomyces griseofuscus*

The desired transformation was performed in substantial accordance with the procedure of Example 8 using 3 µl (about 1.5 µg) of total pooled DNA from part E above. *S. griseofuscus* transformants were selected on R2-agar plates with 25 µg/ml apramycin. Approximately 60,000 transformants were obtained. About 7,000 transformant colonies from one plate were homogenized and grown overnight at 30° C. in 10 ml of TSB with 25 µg/ml apramycin and 0.1 µg/ml spiramycin. The next day, ∼0.5 ml of this overnight culture was plated on TSB-agar plates containing 25 µg/ml apramycin and 25 µg/ml spiramycin. The plates were incubated at 30° C. for 7 days. Apramycin-resistant, spiramycin-resistant transformants were obtained.

The antibiotic resistance spectrum of the above obtained transformants were determined by disc assay as follows. A spiramycin-resistant transformant clone was grown in 5 ml of TSB with 25 µg/ml apramycin at 30° C. overnight. The overnight culture was homogenized and 0.2 ml of the homogenized culture overlaid onto TSB-agar plates containing 25 µg/ml apramycin using 4 ml of a nutrient agar overlay. Macrolide disc pads (20 µg macrolide antibiotic per disc pad) were placed on the hardened overlay and incubated for 3 days at 30° C. The resulting colonies were resistant to picromycin and other macrolides such as erythromycin, lincomycin, spiramycin, and rosamycin but were sensitive to tylosin like *S. felleus*. Four ml cultures of such picromycin-resistant colonies were grown and plasmid DNA was prepared in substantial accordance with the procedure of Example 12 and resuspended in 20 µl of TE buffer. Ten µl of this plasmid DNA was used to transform *E. coli* K12 JM109 in substantial accordance with the procedure of Example 4. Transformants were selected at 37° C. on TY plates containing 200 µg/ml apramycin. The desired transformant containing plasmid pOJ208 was obtained. Plasmid pOJ208 contains ∼35 kb of *S. felleus* DNA.

EXAMPLE 16

Construction of Phasmid pOJ405

A. Construction of Intermediate Plasmid pOJ303

Approximately 5 µg (5 µl) of plasmid pOJ208 DNA as obtained in Example 15, were added to 10 µl of 10× XhoI buffer (500 mM NaCl; 500 mM Tris-HCl, pH 8.0; 100 mM MgCl₂; and 10 mM DTT), 1 µl (about 10 units) of restriction enzyme XhoI, 84 µl of H₂O, and reacted for 2 minutes at 37° C., to obtain a partial digest. The reaction was stopped by heat inactivation at 70° C. for 15 minutes. The DNA was precipitated with ethanol, and resuspended in 20 µl of TE buffer.

Approximately 1 µg (4 µl) of the XhoI(partial) digest of pOJ208 DNA was ligated by incubation at 16° C. overnight with 4 µl of 10× T4 DNA ligase buffer, 1 µl (about 500 units) of T4 DNA ligase and 31 µl of H₂O. The ligation produced the desired intermediate plasmid pOJ303. Ten µl of the 40 µl ligation reaction were used to transform *E. coli* K12 JM109 in substantial accordance with the procedure of Example 4. Transformants were selected at 37° C. on TY-agar plates with 200 µg/ml apramycin.

Plasmid pOJ303 DNA was prepared in substantial accordance with the procedure of Example 12 and used to transform S. griseofuscus in order to test for macrolide resistance as in Example 15.

B. Construction of Intermediate Plasmid pOJ321

Approximately 5 µg (5 µl) of plasmid pOJ303 DNA were added to 10 µl of 10× NcoI buffer (1.5M NaCl; 60 mM Tris-HCl, pH 7.5; 60 mM MgCl₂; and 10 mM DTT), 1 µl (about 5 units) of restriction enzyme NcoI, 84 µl of H₂O, and reacted at 37° C. for 1 hour. After reacting, the DNA was precipitated with ethanol and resuspended in 20 µl of TE buffer.

Four µl of the NcoI-digested plasmid pOJ303 DNA were ligated by incubation at 16° C. overnight with 4 µl of 10× T4 DNA ligase buffer, 1 µl (about 500 units) of T4 DNA ligase buffer and 31 µl of H₂O. The ligation produced intermediate plasmid pOJ321.

Approximately 10 µl of the ligation reaction were used to transform E. coli K12 JM109 in substantial accordance with the procedure of Example 4. Transformants were selected at 37° C. on TY-agar plates with 200 µg/ml apramycin. A culture of E. coli K12 JM109/pOJ321 is on deposit at the National Regional Research Laboratory in Peoria, Ill. under the accession number NRRL B-18389.

Plasmid pOJ321 DNA was prepared in substantial accordance with the procedure of Example 12 and used to transform S. griseofuscus in order to test for macrolide resistance as in Example 15.

C. Construction of Phasmid pOJ405

Approximately 20 µg (20 µl) of plasmid pOJ321 DNA were added to 10 µl of 10× PvuII buffer, 3 µl (about 60 units) of restriction enzyme PvuII, 67 µl of H₂O, and reacted at 37° C. for 2 hours. After reacting, the digestion was electrophoresed on a 1% agarose gel and an ~2.8 kb PvuII fragment was isolated in substantial accordance with the procedure of Example 3B. The fragment was resuspended in 20 µl of TE buffer.

Approximately 5 µg (5 µl) of phasmid pOJ401 DNA prepared as in Example 3 were added to 10 µl of 10× SmaI buffer (60 mM Tris-HCl, pH 7.5; 60 mM MgCl₂; 200 mM KCl; and 10 mM DTT), 2 µl (20 units) of restriction enzyme SmaI, 83 µl of H₂O, and reacted at 37° C. for 2 hours. After reacting, the DNA was precipitated with ethanol and resuspended in 20 µl of TE buffer.

Figure 12:
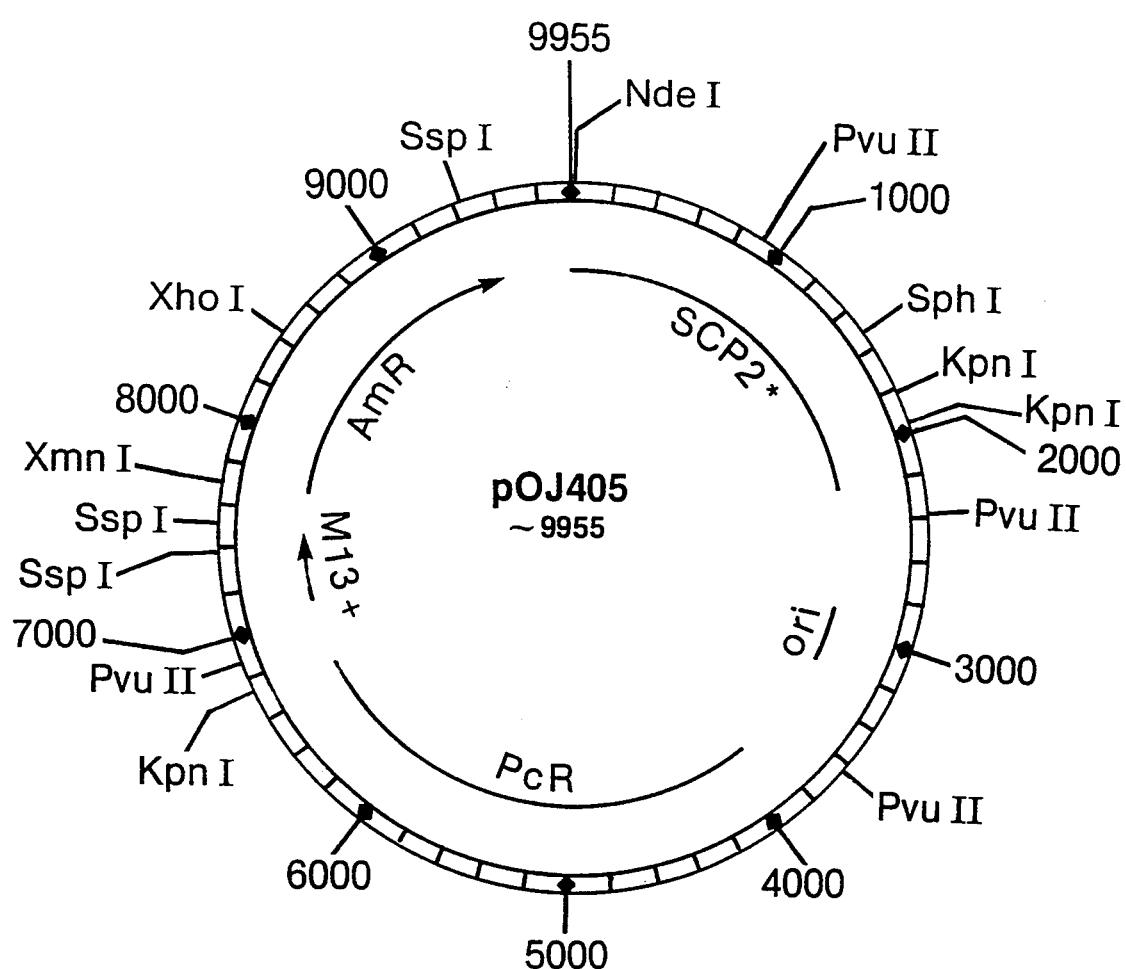
FIG. 12 is a restriction site and function map of phasmid pOJ405.

Approximately 1 µg (5 µl) of the ~2.8 kb PvuII fragment of plasmid pOJ321 and 1 µg (5 µl) of SmaI-digested plasmid pOJ401 DNA were ligated overnight at 37° C. by incubation with 4 µl 10× T4 DNA ligase buffer, 1 µl (about 500 units) of T4 DNA ligase and 25 µl of H₂O. The ligation produced the desired phasmid pOJ405. A restriction site and function map of phasmid pOJ405 is presented in FIG. 12 of the accompanying drawings.

Approximately 10 µl of the ligation reaction were used to transform E. coli K12 JM109 in substantial accordance with the procdure of Example 4. Transformants were selected on TAXI-plates, and plasmid DNA was prepared in substantial accordance with the procedure of Example 1B or Example 12 for use in restriction analysis and for transformation. Phasmid pOJ405 DNA thus obtained was used to transform S. griseofuscus and selection was on R2-agar plates with 25 µg/ml apramycin. The transfer of phasmid pOJ405 into S. griseofuscus conferred the same macrolide resistance phenotype as S. felleus as shown by disc assay. This demonstrated that pOJ401 was a suitable vector into which foreign DNA can be cloned and expressed in Streptomyces, in this instance, a picromycin-resistance gene from S. felleus which confers resistance to a broad range of macrolide antibiotics. Restriction enzyme analysis showed that the transformed S. griseofuscus contained an intact phasmid pOJ405.

We claim:

1. A method of transforming an intact restricting Streptomyces cell using single stranded DNA vectors, said method comprising the steps of:
   (a) producing a DNA phasmid shuttle vector, said vector comprising:
      (i) a replicon that is functional in E. coli,
      (ii) a replicon that is functional in Streptomyces,
      (iii) a DNA segment that contains a replication origin and a morphogenetic signal of a filamentous bacteriophage of E. coli having F pili, and
      (iv) one or more DNA segments that convey resistance to at least one antibiotic when transformed into a sensitive host cell,
   (b) preparing single-stranded DNA of said vector, and
   (c) transforming a restricting Streptomyces host cell with said single-stranded DNA,
   whereby the efficiency of transformation of the restricting Streptomyces host cell with said single stranded vector is approximately equal to or greater than the efficiency of transformation of the same restricting Streptomyces host cell with the double stranded equivalent of said single stranded vector.

2. The method of claim 1 wherein said DNA phasmid shuttle vector is selected from the group consisting of pOJ401, pOJ402, and pOJ405.

3. The method of claim 1 wherein said DNA phasmid shuttle vector is pOJ401.

4. The method of claim 1 wherein said DNA phasmid shuttle vector is pOJ402.

5. The method of claim 1 wherein said DNA phasmid shuttle vector is pOJ405.

* * * * *